United States Patent [19]

Ebersole et al.

[11] Patent Number: 5,695,925

[45] Date of Patent: Dec. 9, 1997

[54] ANALYTE DETECTION BY MEANS OF AN ANALYTE-RESPONSIVE POLYMER

[75] Inventors: Richard Calvin Ebersole, Wilmington; Robert Paul Foss, Hockessin, both of Del.; Michael David Ward, Minnetonka, Minn.

[73] Assignee: E. I. du Pont de Nemours and Company, Wilmington, Del.

[21] Appl. No.: 526,144

[22] Filed: Sep. 5, 1995

Related U.S. Application Data

[63] Continuation of Ser. No. 916,334, Jul. 17, 1992, abandoned.

[51] Int. Cl.$^6$ .............................. C12Q 1/00; G01N 29/18; G01N 33/48; G01N 33/53
[52] U.S. Cl. ..................... 435/4; 435/7.1; 435/7.2; 435/7.4; 435/12; 435/18; 435/34; 435/39; 436/183; 367/157
[58] Field of Search .................... 367/157; 422/68.1, 422/82.01; 435/5, 6, 7.1, 7.2, 7.32, 7.4, 12, 18, 25, 29, 34, 39, 368; 436/527, 183, 807

[56] References Cited

U.S. PATENT DOCUMENTS

| | | | |
|---|---|---|---|
| 4,312,228 | 1/1982 | Wohltjen | 73/597 |
| 4,732,930 | 3/1988 | Tanaka et al. | 524/742 |
| 4,735,887 | 4/1988 | Foss et al. | 430/264 |
| 4,735,906 | 4/1988 | Bastiaans | 436/527 |
| 4,749,762 | 6/1988 | Foss | 526/312 |
| 5,015,843 | 5/1991 | Seitz et al. | 250/227 |
| 5,028,394 | 7/1991 | Lowell, Jr. et al. | 422/58 |
| 5,156,810 | 10/1992 | Ribi | 422/82.01 |
| 5,224,972 | 7/1993 | Frye et al. | 55/18 |

FOREIGN PATENT DOCUMENTS

| | | |
|---|---|---|
| 0 215 669 | 9/1986 | European Pat. Off. . |
| 0 215 669 | 3/1987 | European Pat. Off. ........ H01L 41/08 |
| 0254575 | 1/1988 | European Pat. Off. . |
| 0311768 | 4/1989 | European Pat. Off. . |
| 0402917 | 12/1990 | European Pat. Off. . |
| 3 733 986 | 4/1989 | Germany . |
| 3733986 | 4/1989 | Germany . |
| 63-206653 | 2/1987 | Japan . |
| 63-206653 | 8/1988 | Japan . |
| 2-212744 | 8/1990 | Japan . |
| WO 91/01381 | 2/1991 | WIPO . |
| WO 9210758 | 6/1992 | WIPO . |

OTHER PUBLICATIONS

Ward et al., "In Situ Interfacial Mass Detection with Piezoelectric Transducers", Science, vol. 249, pp. 1000–1007.
Muramatsu et al., "Computation of Equivalent Circuit Parameters of Quartz Cryontact with Liquids and Study of Liquid Properties", Anal. Chem. 1988, 60,2142–2146.
J. Wang et al, "Piezoelectric pH Sensors: AT–Cut Quartz Resonators with Amphoteric Polymer Films", *Anal Chem* (01 Oct. 1993) vol. 65, No. 19, pp. 2553–2562.
Prusak-Sochaczewski et al *Analytical Letters* 23 (3) 401–409 (1990).
Ward, M.D. et al, "In Situ Interfacial Mass Detection with Piezoelectric Transducers", *Science*, 249, 1000–1007 (1990).
Muramatsu, H. et al, "Computation of Equivalent Circuit Parameters of Quartz Cryontact with Liquids and Study of Liquid Properties", *Anal. Chem.*, 60, 2142–2146 (1988).
Wang, J. et al, "Piezoelectric pH Sensors: AT–Cut Quartz Resonators with Amphoteric Polymer Films", *Anal. Chem.*, 65, 2553–2562 (1993).

*Primary Examiner*—Ponnathapura Achutamurthy

[57] ABSTRACT

A composition is provided which is a transducing polymer having from 1 to 20 crosslinks per polymer molecule and selected from the group consisting of amphoteric co- or ter-polymers of pI between 6.2 to 8.0 of acrylic acid, alkyl methacrylate, and N,N-dimethly-aminoethyl methacrylate, the amphoteric co- or ter-polymer immobilized on a surface. Also provided is a method for the preparation of an analyte-responsive polymer immobilized on a surface in which the steps are a. mixing a solution of a crosslinker and the claimed transducing polymer, b. applying the solution of step a to a surface, and c. then curing the polymer to a ratio of from 1 to 20 crosslinks per transducing polymer molecule. Acoustic and optical methods for detecting analtyes are also provided which use an analyte-responsive polymer.

3 Claims, 8 Drawing Sheets

ANALYTE DETECTION BY MEANS OF AN ANALYTE-RESPONSIVE POLYMER

This is a continuation of application Ser. No. 07/916,334 filed Jul. 17, 1992, now abandoned.

TECHNICAL FIELD

The invention relates to a method of detecting an analyte in a liquid sample that utilizes the acoustic and light energy propagational properties of a polymer interfaced with a sensor.

BACKGROUND

Detection mechanisms capable of detecting chemical and biological substances in the nanomolar range are finding increasing utility in a variety of commercial fields including the food, healthcare, environmental and waste treatment industries. A number of sensitive devices have been developed to meet these detection needs, including those taking advantage of shifts in resonant frequency such as piezoelectric transducers as well as optical sensors which operate on the basis of changes in refractive indices.

The ability of piezoelectric transducers to detect small changes in mass, viscosity and density at their surfaces while immersed in liquids has made them particularly useful as analytical tools where the measurement of very small amounts of material must be made in solution. Design strategies for piezoelectric sensors have primarily involved events that result in mass changes at the surface of the crystal. The most extensively studied transducer in this regard has been the shear mode AT-cut quartz resonator, commonly referred to as the quartz crystal microbalance (QCM), which comprises an AT-cut quartz crystal sandwiched between two metal excitation electrodes. An example of the use of the QCM used to detect biological analytes is seen in EPO Patent Publication No. 0 215 669 (Karube et al.) where the concentration of an analyte in solution was calculated on the basis of the change in resonance frequency ($\Delta f$) caused by the weight of an analyte added to a receptor material immobilized on the surface of a piezoelectric device. The invention of Karube demonstrated that the piezoelectric transducer was useful in measuring the concentration of some biological analytes.

Although a useful tool in solution environments, a piezoelectric transducer must have its surface modified in order to give it a measure of specificity for the analyte to be detected, and preparation of these modified piezoelectric devices is procedurally complex and often difficult. In cases where the analytes to be detected are biological in nature, receptor agents (antigens, antibodies or other ligands) must be immobilized on the surface of the crystal. This method has significant inherent limitations; however, as the receptor agents can inactivate during the immobilization process or separate from the surface of the crystal after immobilization.

To facilitate receptor modification of the QCM, polymer coated quartz oscillators have been developed that that allow for more efficient and specific binding of receptor agents. Muller-Schulte (DE 3733986 A1) describes the coating of a piezoelectric oscillator with a water-insoluble polymer that facilitates the adsorbtion of various biomolecules. These immobilized biomolecules can then bind antigens or ligands and the resulting increase in mass of the oscillator quartz translates into changes in resonant frequency which can be used to quantitate the analyte.

These examples of the use of the piezoelectric sensors are useful but limited in that they all rely on a mass change on the sensor surface to effect a change in resonant frequency. Sensor design based solely on mass changes can be limiting if the analytes have low molecular mass. For example, the mass increase associated with the binding of a protein to an active surface of a shear mode AT-cut crystal generally will not be sufficient for a practical frequency response. Other considerations include the rigidity of the bound analyte; for example, Newtonian films that bind to the surface of a QCM give frequency shifts that are much smaller than predicted by the Sauerbrey equation (Sauerbrey, Phys. (1959) 155:206).

Additionally, piezoelectric oscillator techniques have not been well-suited to continuous real-time (kinetic) measurements of the biological activity of organisms and the usefulness of receptor-modified piezoelectric methods has been limited by the specificity of known reagents, a fact that requires repeated testing to assess the presence of different organism types.

To overcome these limitations, polymer films have been designed to react with specific reagents, ions or metabolites in an attempt to increase the specificity of the detection method. For example, U.S. Pat. No. 4,735,887 (Foss et al.) discloses that propyleneimine will react with polyampholytes via a ring-opening mechanism to form primary amines. The primary amines can react with tanning developers and with ordinary aldehyde crosslinking agents to form crosslinked networks. Ebersole et al. (Int'l. Pub. No. WO 91/01381) describe the use of polyampholytes in solution which, upon contact with the metabolic products of an organism, deposit upon a piezoelectric device to produce a change in resonance frequency that is correlated to the concentration or rate of change in the presence of a metabolic product. Here the polyampholyte is not immobilized on the surface of the sensor before exposure to an analyte suspected of being present in a sample. Tanaka et al. (U.S. Pat. No. 4,732,930) have demonstrated that certain ionic gels formed by the polymerization of isopropylacrylamide in the presence of a metal ion containing monomer, crosslinking agent, and a suitable liquid medium are capable of drastic volume changes in response to changes in solvent composition, temperature and pH or ion composition. Tanaka et al., however, make no attempt to link the nature of these gels to a measuring device utilizing piezoelectric oscillators or detection of changes in refractive indices to achieve analyte sensitivity.

Attempts to integrate the dynamic physical dimensional properties of polymer films into analyte detection systems have been few and poorly developed. Various physical dimensional changes have been reported for crosslinked polymers responding to changes in partial pressures of gases such as oxygen (Irani et al., Flammability and Sensitivity of Materials in Oxygen-Enriched Atmospheres: Third Volume, ASTM STP 986, D. W. Schroll, Ed., American Society for Testing and Material, Philadelphia, (1988) pp 346–358) as well as to changes in humidity and salt concentrations. JP 63-206653 describes a salt concentration sensor characterized by the fact that an organic polymer gel layer or mass is retained on a support which gives rise to a change of phase or a change in volume depending on the salt concentration. JP 2-212744 describes a semiconductor humidity sensor which detects atmospheric humidity on the basis of the expansion or contraction of a moisture-sensitive polymer in contact with the surface of a piezoelectric cell. Changes in the piezoresistance of the cell are translated into percent atmospheric humidity.

Although gels and crosslinked polymers are known to be responsive to various biological and ionic analytes as shown in the above art, in all cases the preparations depend on a common physical principle of polymer swelling in response to salt or humidity changes. Furthermore, there is nothing inherent in the polymer gel that makes it specifically responsive to water or a particular ion and all gels must be in a pre-swollen state in order to function.

Optical sensors for the detection of analytes generally rely on small changes in the indices of refraction in response to the presence of an analyte. Commonly used optical sensors include planar waveguides, optical fibers and diffraction gratings. In general, optical sensors of this sort suffer from many of the same disadvantages as piezoelectric oscillators such as lack of specificity for an analyte, difficulty in surface preparation as well as difficulty in measuring continuous real-time (kinetic) changes in biological activity. To date, these difficulties in the field of optical sensors remain unaddressed.

There remains a need therefore for a novel analyte-responsive polymer that (1) responds to the presence of an analyte by altering its ability to propagate light and/or acoustic energy, (2) exhibits a specificity for a particular analyte, and (3) retains the ability to form a composite with the surface of a sensor such that the changes in the propagational properties are detected by the sensor.

SUMMARY OF THE INVENTION

The subject matter of the invention includes as one aspect a method relying on the acoustic and/or light energy propagational properties of an analyte-responsive polymer for detecting an analyte. The method comprises:

a. contacting either an acoustic or optical detection system with an analyte to which an analyte-responsive polymer contained in the detection system is responsive;

b. in the case of an optical embodiment of the invention, interfacing the system of step a with a means to detect changes in the light propagation of the analyte-responsive polymer;

c. measuring propagational changes in the properties of the detection system; and d. correlating the propagational changes measured in step c with the presence, concentration, or rate of production of the analyte.

Another aspect of the invention is a composition of matter comprising a transducing polymer having from 1–20 crosslinks per polymer molecule and selected from the group consisting of amphoteric co- or terpolymers of pI between 5.0 to 8.0 of acrylic acid, alkyl methacrylate, and N,N-dimethyl-amphoteric methacrylate, the amphOteric co- or terpolymer immobilized on a surface. A further aspect of the invention is the method of making the composition claimed.

DETAILED DESCRIPTION OF THE INVENTION

Figure 1:
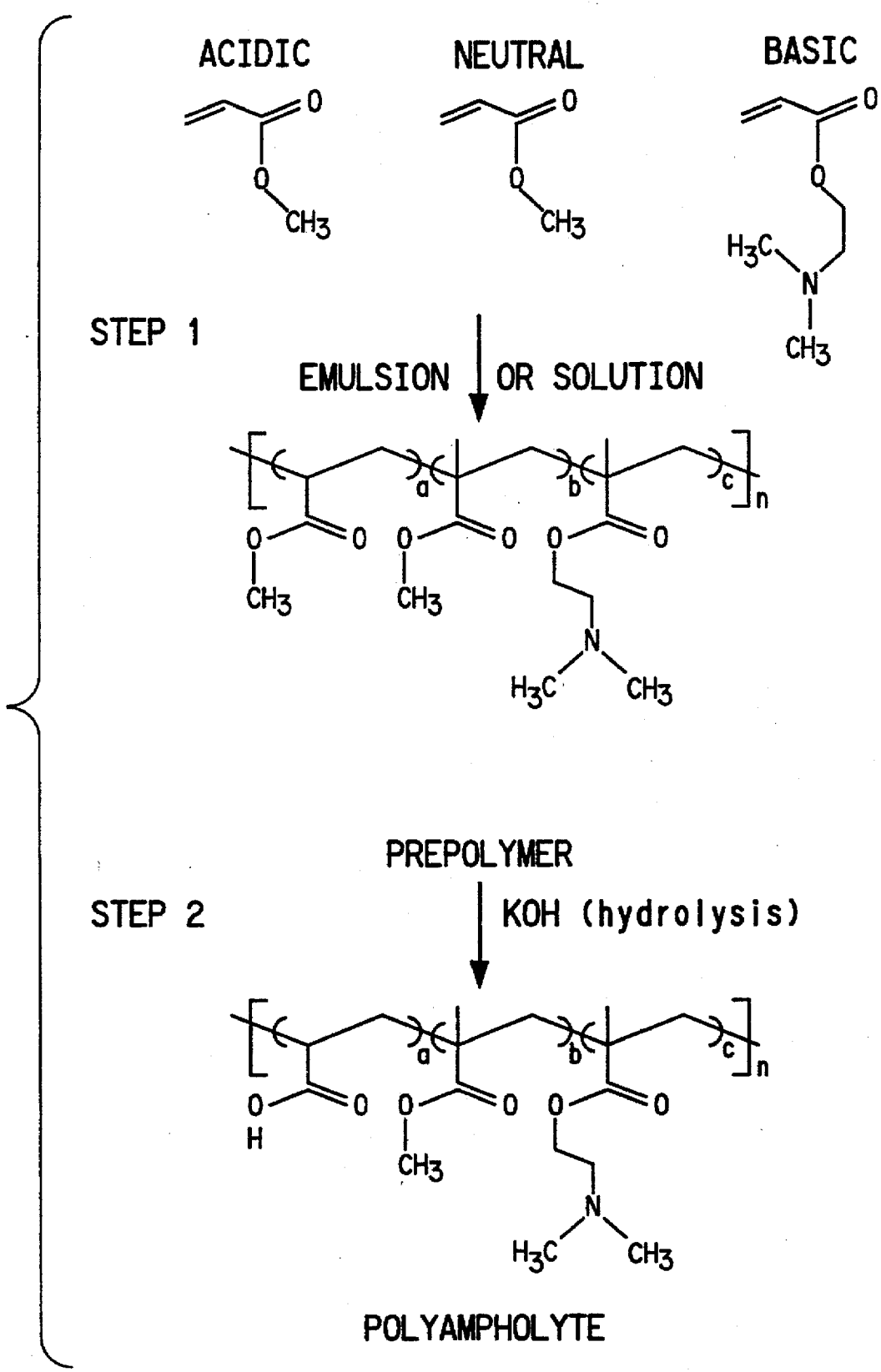
FIG. 1 illustrates the two-step polyampholyte preparation process.

Applicants have invented a method of detecting specific analytes in solution via a mechanism that makes use of the inherent propagational properties of crosslinked polymer films.

The precise nature of the changes in the propagational properties is not fully understood, but it is tentatively attributed to changes in the viscoelasticity, rigidity and acoustic and light wave propagational abilities of the analyte-responsive polymer film. Although changes in mass may occur, it is understood that the invention does not measure a weight gain. Rather, the invention hinges on the resulting polymer-analyte complex having propagational properties different from that of the original transducing polymer. These propagational changes are detected by sensors with which the polymer-analyte complex is associated. The changes may be quantitatively correlated to the amount of analyte present.

The inventive subject matter also includes unique compositions of crosslinked polymers immobilized on the surface of a sensor. The polymers may or may not contain receptors specific to particular analytes, such as ions, ligands, antibodies, etc. In the specific case of detection of hydrogen ions, impedance analyses of certain insoluble films of a crosslinked analyte-responsive polymer indicate changes in the polymer film properties when the pH of the medium is changed. When such a polymer is immobilized on the surface of a quartz microbalance, the resonant frequency of the polymer/quartz composite resonator decreases significantly in the isoelectric region. The resonant equivalent resistance and bandwidth increases upon approaching the pI, but decreases at the pI to values near those observed for the ionic forms. At pH extremes where the polymer is either fully protonated (cationic) or fully deprotonated (anionic), the polymer is swollen due to electrostatic repulsion between sites with similar charges. Conversely, at the pI the polymer is less swollen due to electrostatic crosslinking in the films. The changes in swelling and the attendant changes in viscoelastic properties and acoustic and light wave propagation produce unexpectedly large frequency changes.

The invention describes two approaches to detecting changes that occur in a thin polymer film due to the influence of an analyte, in which the polymer film is coated on either a piezoelectric acoustic wave device or on a device capable of measuring changes in refractive indices of the polymer film. The principle of transduction for the two approaches is similar in that both rely on analyte-induced changes in the propagation of waves in the polymer film. This can be illustrated with a thickness shear mode acoustic wave device, for example an AT-cut quartz crystal coated with the polymer film, the combination thereof herein referred to as the composite resonator. The acoustic wave propagates back-and-forth through the thickness of the quartz crystal, across the polymer film-quartz interface and through the polymer film. This results in the establishment of a standing wave in the composite resonator with a frequency corresponding to the resonant frequency. The resonant frequency is determined by the thickness of the composite resonator and the propagation velocity of the acoustic wave. The energy attenuation of the acoustic wave is affected by viscous losses encountered by the acoustic wave during propagation. Since the thickness, propagation velocity, and energy attenuation in the quartz crystal are not affected by the analyte, the composite resonator is sensitive only to analyte-induced changes in the properties occurring in the polymer film. The resonant frequency is therefore affected by analyte-induced propagational changes and the modulus of the polymer film, and the energy attenuation by loss in the viscosity of the polymer in the polymer film. That is, the energy attenuation depends upon the amount of energy "reflected" back into the composite resonator during oscillation. This is customarily defined as the quality factor Q, which is the ratio of energy stored to energy lost during oscillation of the resonator. Increasing energy attenuation results in lower values of Q, higher values of the equivalent resistance R and increases in the bandwidth of the electrical conductance.

The optical sensing approach is similar in that light waves propagate back-and-forth across the polymer film interfaced with a support and into the polymer. In essence, a standing wave is established in the composite optic sensor. The standing wave may be a single frequency, or more commonly, a range of frequencies. The amount of light reflected back into the detector depends upon the refractive index of the polymer film. Since the refractive index of the support is independent of the analyte, changes in the refractive index of the polymer film due to the influence of analyte are responsible for changes in the amount of light reflected back and ultimately detected by the optic sensor. The resulting changes in the light intensity are therefore analogous to the changes in the energy attenuation in the acoustical wave device. The two devices are related conceptually in that both are sensitive to changes in the transmission of wave energy resulting from the influence of the analyte on the polymer film properties. In addition, it is feasible that specific wavelengths of light can be absorbed by the polymer film, and the degree of absorption can be influenced by the analyte interaction with the polymer. This can result in changes in the intensities of different wavelengths, therefore changing the weighted average frequency of light exiting the sensor. This is analogous to the changes in the resonant frequency detected in the acoustic wave device. Both devices therefore are similar conceptually when described according to principles of wave propagation.

In support of the disclosure of this invention, the following terms are intended to convey the following meanings.

"Analyte" ("A") means any substance capable of interaction or reaction with an analyte-responsive polymer, including analyte-responsive polymers containing Biological Receptors. The Analyte may be formed or consumed by chemical or biological processes, including the growth and metabolic processes of cells, microorganisms or their subcellular components. The Analyte may be free-floating in a media, attached to a cell surface, contained within a cell, or produced on the surface of the analyte-responsive polymer as a result of enzyme catalysis. The Analyte alternatively may be the product of catalytic reactions, enzyme immunoassays, or DNA probe assays. The Analyte may be an acid, buffering agent, salt, enzyme, protein, carbohydrate, lipid or similar biological product or a substance that is diminished or increased in concentration by biological activity.

"Biological Receptors" are substances that form specific binding pairs with the Analyte. These may variously be chelating agents, antibodies, lectins, tissue receptors, cellular adhesion factors, ligand binding proteins and similar analyte receptor reagent substances.

"Transducing Polymer" means any polymer that, as the result of interaction with an Analyte, exhibits a change in the properties governing its behavior in the propagation of acoustic or light energy. The transducing polymer may or may not be amphoteric.

"Analyte-Responsive Polymer" ("ARP") means a crosslinked amphoteric polymer that 1) is capable of selective interaction or reaction with an Analyte, and 2) exhibits a change in the properties governing its behavior in the propagation of acoustic or light energy as the result of interaction with an Analyte. The ARP may contain a Biological Receptor capable of forming a specific binding pair with an Analyte.

The polymer is chosen or designed to react with a analyte through a variety of reactions including ion pairing, complexation reactions, redox reactions, or covalent coupling. This adaptability enables the invention to apply equally well to large or small molecular weight analytes.

"Amphoteric Polymer" means an analyte-responsive polymer (either natural or synthetic) which contains both acidic and basic groups. Amino acids and proteins are amphoteric since they contain both acid (—COOH) and basic (—NH$_2$) groups.

"Polymer-Analyte Complex" ("C") means a complex formed upon the reaction or interaction of an Analyte with an Analyte-Responsive Polymer or Amphoteric Polymer. For convenience, "complex" as used herein refers to the substance resulting from the reaction of a analyte-responsive polymer with an analyte regardless of the the specific mechanism involved.

"Propagational Changes" means changes in properties of the analyte-responsive polymer as a result of the polymer's complexation or reaction with an Analyte which may involve, as compared to that of the polymer alone, 1) changes in its ability to propagate either acoustic or light energy or 2) changes in the rigidity, elasticity and/or the viscosity of the polymer-analyte complex, or 3) any alteration in the phase composition of the polymer. The propagational changes in the polymer-analyte complex may be heterogeneously distributed in micro-domains on or within the attached polymer or may be homogeneously distributed on or in the polymer matrix.

"Sensor" ("S") refers to a device to detect propagational changes in the polymer coating material. Piezoelectric oscillator, quartz crystal microbalance and QCM are names for devices that use piezoelectric principles as the basis for detecting such changes. In addition, shear horizontal acoustic plate mode devices (SHAPM) are alternative devices for use in detecting these changes. A waveguide optical biosensor (WB) can be used to detect changes in light propagation properties of the complex. The transducing polymer is applicable to both planar and fiber (cylindrical) wave guide formats including fiber optics, interferometers, refractometers, Mach-Zender and optical grading devices.

"QCM" refers to a bulk acoustic wave device operating in the shear mode typically comprising either AT or BT cut quartz where the quartz is sandwiched between two excitation electrodes.

"Impedance Analysis" refers to any analysis technique that measures the current across the surface of a quartz crystal at a constant voltage over a specified range of frequencies.

"Composite Sensor" refers to the unit of an analyte-responsive polymer film bonded to the surface of a sensor.

"Detection System" refers to the unit of the analyte-responsive polymer, sensor, and test medium.

"Organism" is meant to include any organism which, as a result of its metabolism, makes a product unique to that organism that can be detected or identified by the method of this invention. The organisms for which this invention will be most useful, however, are microorganisms normally grown in aqueous cultures, such as bacteria, fungi, and tissue cells.

"Growth Regulators" are substances that stimulate or retard the growth of the organism.

"Nutrients" are substances metabolized by the organism and necessary for its growth.

The term "XAMA-7®" will refer to any pure chemical composition of pentaerythritol-tris-(B-aziridinyl) propionate. XAMA-7® is a registered trademark of the Virginia Chemical Co.

The crosslinked analyte-responsive polymer (ARP) contains analyte-sensitive moieties and is attached to the surface of a sensor forming a Composite Sensor. A sample of test medium suspected of containing an Analyte is brought into contact with the sensor and any Analyte present interacts or reacts with the ARP to form a polymer-analyte complex. A propagational change is detected in the complex as compared to that of the uncomplexed ARP. The change is manifested as a change in resonance frequency of a piezoelectric oscillator or as a change in light propagation properties by a waveguide optical sensor or other optical detection device.

The invention is particularly useful for the monitoring of biological systems to detect or determine changes in the concentrations of a variety of substances including cellular metabolites, the products of enzymatic reactions, pharmaceutical compositions, industrial chemicals, or any product of a biological system that requires continuous real-time (kinetic) measurement. This invention is also capable of detecting any organism which, as a result of its metabolism, makes or uses a product characteristic of that organism that can be detected or identified by the method of this invention. The invention can be used to detect organisms normally grown in aqueous cultures, such as bacteria, fungi, and tissue cells. However, it is not necessary that these organisms remain intact. The invention is intended to operate as well with disrupted or solubilized components of the organism.

A more specific illustration of the invention is the use of a polymer designed to react with analytes produced as a result of pH changes.

An example of such an analyte is an $H^+$ group. When metabolic organic acids or carbon dioxide produced by organisms acidify the growth medium, protons (analytes) released as the metabolic products react with proton receptor groups on the analyte-responsive polymer, thereby altering the acoustic propagation properties of the polymer. The changes in propagation occur as the pH of the medium approaches the isoelectric point of the complex. This propagational change in the ARP effects a change in the resonant frequency of the piezoelectric oscillator that can be read electronically to determine the metabolic rate and cell growth rate of a culture. Alternatively, reaction of the protons with the polymer can be detected by a waveguide optical sensor or other optical detection device as a change in light propagation properties.

The selectivity of the polymer/analyte interaction also can be controlled by the design of the polymer. For example, antibodies, polynucleic acids, receptors, chelating agents, cellular adhesion factors, and ligand binding molecules can be linked to the polymer. By varying the composition of these receptor sites on the polymer, the invention can be made highly selective for a specific analyte or broadly responsive to a number of analytes.

A more specific illustration demonstrates the analyte selectivity of the invention. A good example is an antigen which complexes with an ARP constructed to contain the complementary antibody as a Biological Receptor. Changes in the amount of crosslinking of the resulting antigen/antibody-polymer complex induce a propagational change in the ARP and produce a change in the resonant frequency of the piezoelectric biosensor. As in other examples, monitoring of the resonant frequency of the piezoelectric oscillator provides a specific measurement of the amount of metabolite or the rate of metabolite production in the medium. Measurements may also be made by means of a light propagational or optical sensor.

Piezoelectric Oscillator

The ability of piezoelectric transducers to detect small changes in mass, viscosity and density at their surfaces while immersed in liquids is well known in the art (Ward et al., Science (1990) 249:1000–1007 and Frye et al., Appl. Spectroscop. Rev. (1991) 26:73). In addition, shear surface acoustic, flexure and shear-horizontal acoustic plate mode devices can be appropriately modified for use as sensors (Lu and Czanderna, Eds., Elsevier, New York, (1984) pp. 351–388 and Guilbault et al., CRC Crit. Rev. Anal. Chem. (1988) 19:1, and Wohltjen et al., ACS Symp. Ser. (1989) 403:157). Most applicable to the present invention is the shear mode AT-cut quartz resonator, commonly referred to as the quartz microbalance (QCM), which comprises an AT-cut quartz crystal sandwiched between two metal excitation electrodes which generate a standing shear wave across the thickness of the quartz crystal. The shear wave experiences an antinode at the surface of the quartz crystal and propagates into the film on the surface of the crystal; the thickness of the film and the nature of the shear wave propagation in the film determine the frequency response. The frequency response of the QCM generally is interpreted in terms of a mass increase on the resonator surface, which causes a corresponding decrease in the resonant frequency according to the Sauerbrey relationship (Sauerbrey, Phys. (1959) 155:206) (eq. 1), where $\Delta f$ is the measured frequency shift of the initial (resonant) frequency (f) of the quartz crystal, $\Delta m$ is the mass change, A is the piezoelectrically active area defined by the two excitation electrodes, Pq is the density of quartz (2.648 g/cm$^{-3}$) and Uq is the shear modulus (2.947×10$^{11}$ dynes cm$^{-2}$ for AT-cut quartz).

$$\Delta f = 2f_0^2 \Delta m \sqrt{A P_q U_q}\ \ 2f_0^2 \Delta m \quad \text{(eq. 1)}$$

Surface acoustic wave (SAW) and shear horizontal acoustic plate mode (SH-APM) devices represent an alternative piezoelectric transduction techniques applicable to this invention. These devices comprise interdigitated microelectrode arrays on the surface of a piezoelectric quartz substrate. They exhibit frequency changes that can be correlated with mass changes or stiffness coefficient at their surface arising from changes in the velocity of a transverse surface wave. These devices have also been employed as viscosity sensors.

Optical Sensors

The use of optical biosensors to detect the presence of various analytes is common and many examples may be found in the art. (Place et al., Optical-Electronic Immunosensor: "A Review of Optical Immunoassay at Continuous Surfaces", Biosensors, 1, 321–353). Suitable types of optical sensor devices include planar waveguides (Burgess, Proc. SPIE-Int. Soc. Opt. Eng., 1368 (Chem., Biochem., Environ. Fiber Sens. 2), 224–9 (1991)), optical fibers (Bluestein et al., "Fiber Optic Evanescent Wave Sensors for Medical Diagnostics", TIBTECH, 8, 161168 (1990)), metalized prisms (Kooyman et al., "Surface Plasmon Resonance Immunosensors", Analytical Chem. Acta., 213, 35–45 (1988)) and diffraction gratings. The detection surfaces of optical sensors can be planar or cylindrical (fibers).

Generally, optical biosensors respond to small changes in the index of refraction at the surface of a waveguide. This change in the index of refraction results from the selective binding of an analyte to an immobilized analyte-receptor on the surface of the optical sensor. Light traveling in the waveguide induces an evanescent wave in the test media above the waveguide. The interaction of this evanescent wave with analyte/receptor complexes alters either the intensity of the evanescent wave or the coherency of light propagated in the waveguide. Evanescent wave intensity can be altered by changes in fluorescence, adsorption, or light scattering properties of the resulting analyte/receptor complexes. In this way the formation of an analyte/receptor complex can alter the light intensity. Alternatively, the phase or coherency of light traveling through single mode waveguides can be altered by the analyte/receptor interaction and the changes in phase or coherency resulting from the analyte/receptor interaction measured by interferometric devices (e.g., Mach-Zehnder).

Analyte-Responsive Polymers

Polymers used in preparation of an analyte-responsive polymer matrix are polyampholytes containing both acid and base functionalities and having a defined isoelectric point (pI). Polyampholytes of both synthetic and biological origins can be used and can be comprised of both synthetic (e.g., acrylic, etc.) or biological (e.g., aminoacids, etc.) monomers. The polyampholytes have a molecular weight generally in the range of 500 to 500,000 and more preferably, in the range of 1000 to 100,000. The analyte specific polymer is formed by crosslinking the polyampholytes, forming an analyte responsive polymer matrix having a crosslinked density of 1 to 20 cross-linkers per polymer molecule and having a thickness ranging from monomolecular to several microns, and more preferably from 0.05 to 5 microns.

Specific polymers used as analyte-responsive polymers for the examples of a sensing device using acoustic or light energy are co- or terpolymers of acrylic acid (AA), alkyl methacrylate (RMA), and N,N-dimethylaminoethyl methacrylate (DMAEMA). Structurally, the polymers may be linear or may contain pendent or crosslinking chains. They are prepared using a two-step process outlined in U.S. Pat. No. 4,749,762 herein incorporated by reference. The first step produces a prepolymer from methyl acrylate (MA), RMA and DMAEMA. The second step is the controlled selective hydrolysis of methyl acrylate segments to form a product with pendant acid and base groups. FIG. 1 illustrates the two-step polyampholyte preparation process. Other synthetic methods, including Group Transfer Polymerization (GTP), may also be incorporated in preparation of amphoteric polymers.

A two-step emulsion process is preferred over direct solution polymerization for the following reasons. Michael addition of the amine to acrylic acid monomer is more easily prevented. Emulsion polymerization of prepolymer is significantly faster and more easily controlled than solution polymerization. In addition, the composition distribution of monomer units in the polymer is far more easily regulated by controlled feed methods. The polymers are generally soluble in water at all pH's other than their isoelectric points (pI). The isoelectric point is determined by the ratio of acid to base groups and thus can be varied by synthesizing polymers with appropriate ratios. The preferred ratio for monomers used in the instant invention is such that the polymer's pI is in the physiological region (pH ~6.2–8.0). This normally corresponds to a ratio of acid to base of 2.0 to 0.8 for acrylic acid and DMAEMA. (The pI is necessarily dependent on the pKa values for the component groups.) Responses can also be affected by the nature and size of the neutral, non-ionic segment, which can influence the pK of the component acid and base moieties. The solubility characteristics of the polymers are strongly influenced by their ion content. Polymers having significant neutral hydrocarbon segments are less water-soluble at their isoelectric point than polymers with few or no neutral segments. Applicants have prepared a series of polymers containing different alkyl methacrylates and having variable segment fractions, all with pI's in the physiological range. Several other polymers having different solubility and associative characteristics are also predicted to be suitable. Some of these polymers are listed in Table A.

TABLE A

POLYAMPHOLYTES FOR DETECTION OF BACTERIA GROWTH

| Composition (M.V.) | Molar Ratio* | | pI | M.W. |
|---|---|---|---|---|
| | Est.* | Calc. from C, H, N | | |
| AA-MMA-DMAEMA (—) | 1-1-1 | — | 6.53 | — |
| AA-MMA-DMAEMA (12200) | 1-1-1 | 1.05/1.36/1 | 7.63 | 14800 |
| AA-MMA-DMAEMA (35800) | 1-1-1 | 1.014/1.12/1 | 6.95 | 45300 |
| AA-MMA-DMAEMA (30200) | 1-1-1 | 1.03/1.21/1 | 7.39 | 38700 |
| AA-MMA-DMAEMA (30300) | 1-2-1 | 1.06/2.46/1 | 7.11 | 39400 |
| AA-EMA-DMAEMA (70700) | 1-1-1 | — | 7.30 | 100000 |
| AA-BMA-DMAEMA (224000) | 1-1-1 | 1.083/1/1 | 7.50 | 350000 |
| AA-MMA-DMAEMA (68400) | 1-3-1 | 1.035/3.38/1 | 7.46 | 99000 |
| AA-MMA-DMAEMA (36000) | 4-5-1 | 4.69/6.36/1 | 5.37 | 45600 |
| AA-MMA-DMAEMA (67800) | 2-3-1 | 2.08/3.25/1 | 6.57 | 97200 |
| AA-MMA-DMAEMA (136000) | 1-3-2 | 1/3.22/2 | 8.14 | 204000 |

Figure 2:
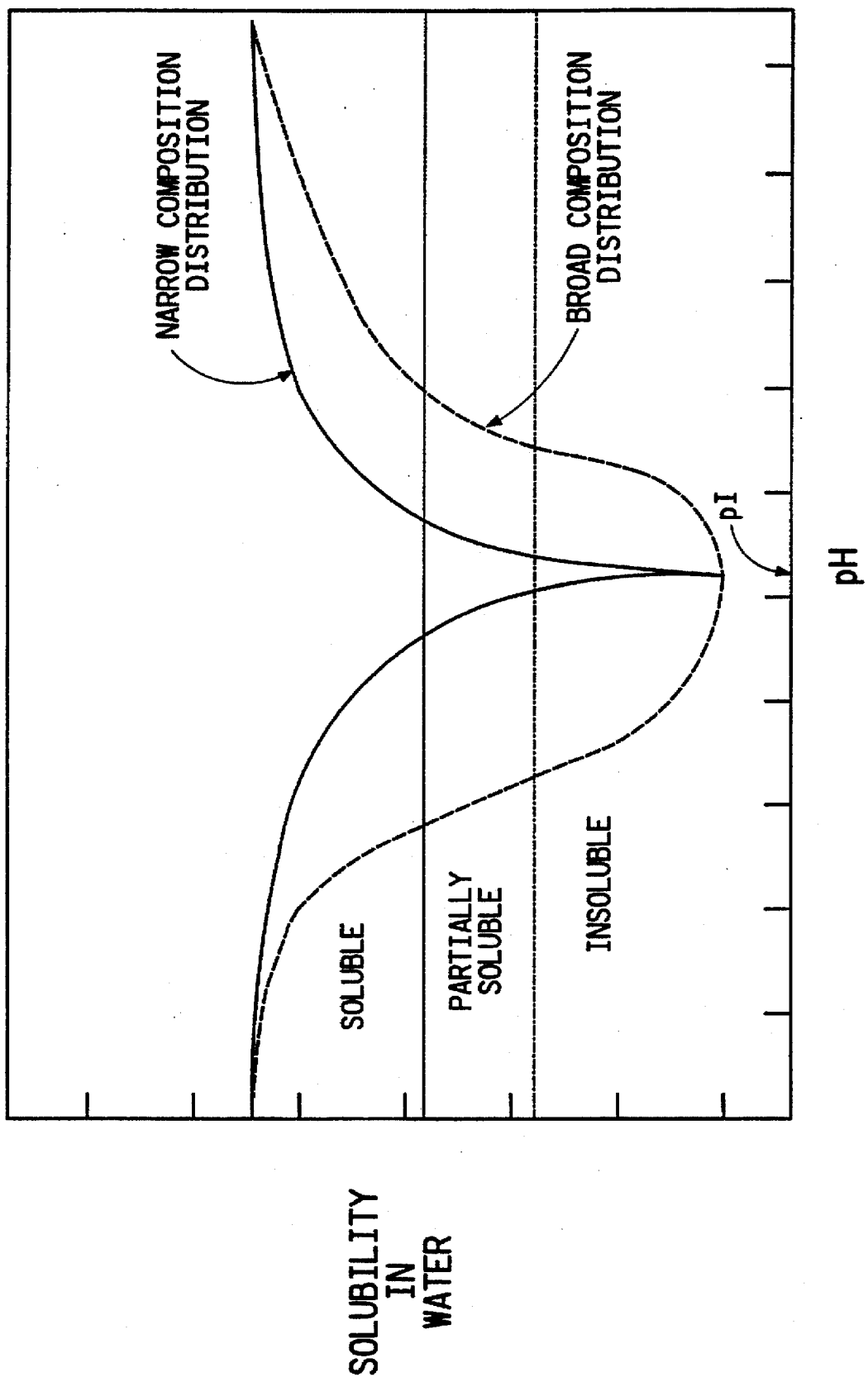
FIG. 2 is a graph showing the effect of reaching the pI of materials with narrow and broad composition distributions.

AA = acrylic acid
RMA = alkyl methacrylate
DMAEMA = N,N-dimethylaminoethyl methacrylate
MA = methyl acrylate
EMA = ethyl methacrylate
BMA = butyl methacrylate
MMA = methyl methacrylate
$M_w$ = Weight-average molecular weight
$M_v$ = Viscosity-average molecular weight
*Approximate mole ratios listed The sensitivity of the polymer to small changes in pH is largely dependent on the narrowness of its composition distribution. This is represented in FIG. 2. A narrow composition distribution is generated by controlling the ratio of reacting monomer in the reaction medium. This ratio is not that found in the polymer but is determined by the reactivity ratios of the constituent monomers. The ratio can be maintained by using either a balanced feed or a starved feed reaction process. The balanced feed process described in the U.S. Pat. Nos. 4,735,887 and 4,749,762, incorporated herein by reference, requires careful reaction control, but leads to rapid formation of high molecular weight product. The starved feed process is preferable when rapid production of high molecular weight product is unnecessary. The starved feed process involves the addition of feed monomer at a rate much lower than its bulk reaction rate in neat media. The reaction becomes essentially a living free radical process, occurring only when monomer encounters an emulsion particle containing a living radical. Enough "balance monomer" is added to saturate the aqueous phase (determined as the point where the solution starts to develop translucence), before starting addition of initiator. A slight excess of MA should also be maintained to give the correct product composition. This is easily accomplished because of the favorable relationship between total inherent reaction rate and reactivity ratios for the acrylate-methacrylate system. Many combinations of monomer are capable of yielding polymers having pI's in the physiological pH range. Amphoteric polymers can be prepared from various combinations of the following sets of monomers set out below:

A. Acidic monomers-Molecular or ionic substance that can yield a hydrogen ion to form a new substance. Examples are acrylic acid, methacrylic acid, and monomers containing phosphoric acid and sulfonic acid groups.

B. Basic monomers-Molecular or ionic substance that can combine with a hydrogen ion to form a new compound. Examples are DMAEMA, diethylaminoethyl methacrylate, t-butylaminoethyl methacrylate, morpholinoethyl methacrylate, piperidinoethyl methacrylate.

C. Neutral monomers-Molecular or ionic substance that is neither acidic or basic. Examples are alkyl methacrylates (methyl MA, ethyl MA, butyl MA), hydroxyethyl methacrylate (HEMA), hydroxypropyl methacrylate, vinyl pyrrolidone, vinyl acetate (vinyl alcohol on hydrolysis), acrylamides, vinyl ethers, styrene. (Reaction of co-monomers having vastly differing reactivity ratios requires very careful reaction control and therefore is not preferred.)

In addition to the examples set out above and in Table A, any aqueous soluble amphoteric polymer with a pI in the physiological range may be useful as a pH sensitive analyte-responsive polymer. Specific examples include:

1) Polymers generated by the reaction of dimethylamino ethanol and similar compounds with methylvinylether/maleic anhydride co-polymers.

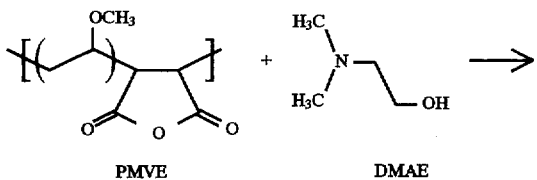

PMVE    DMAE

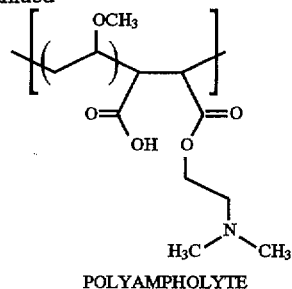

POLYAMPHOLYTE

2) Hydrolyzed co-polymers of vinyl pyridine and methyl acrylate

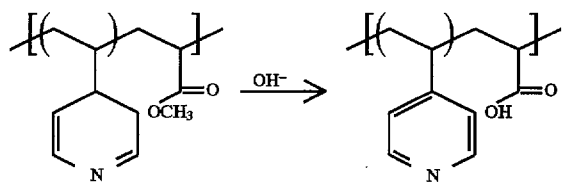

Optionally, the analyte responsive polymer may contain an analyte receptor reagent capable of selective analyte binding. The receptor reagents can be chemically linked to pendent functional groups (such as hydroxyl, carboxyl, amino, thiol, aldehyde, anhydride, imide and epoxy) on the polymer or immobolized within the analyte responsive layer by means of entrapment within the polymer matrix. Alternatively, the analyte receptor reagents could be immobilized by adsorptive interactions with the polymer or a polymer matrix component. This forms an intermediate group that is reactive towards the analyte. In the assay, the analyte attaches to the activated polymer by reaction with the intermediate coupling group.

A wide variety of analyte receptor reagents are contemplated. These include one member of an analyte specific binding pair. Members of specific binding pairs may be of the immune or nonimmune types. The immune types include antibodies, whether polyclonal, monoclonal or an immunoreactive fragment such as Fab-type, which are defined as fragments devoid of the Fc portion of the antibody (e.g., Fab, Fab' and f(ab')$_2$ fragments or so-called "half-molecule" fragments obtained by reductive cleavage of the disulfied bonds connecting the heavy chains). If the antigen member of the specific binding pair is not immunogenic (e.g., a hapten) it can be covalently linked to a carrier protein to render it immunogenic. Polynucleic acids and receptors are also contemplated as analyte receptor reagents.

Non-immune binding pair members include systems wherein the two components share a natural affinity for each other but are not antibodies. Exemplary non-immune analyte receptor reagents include avidin, streptavidin, complementary probe nucleic acids, binding proteins, chelation reagents, cellular adhesion factors and ligand binding proteins.

Linking chemistry for the attachment of analyte receptor reagents involving glutaraldehyde, cyanogen bromide, hydrazine, bisepoxirane, divinylsulfone, epichlorohydrin, periodate, trichlorotriazine, diazonium salts, carbonyldiimidazole, carbodiimides, N-hydroxy succinimide, and tosylates has been described extensively in the art. A review of these chemistries and procedures is given in "Practical Guide for Use in Affinity Chromatograph and Related Techniques", Reactifs IBF-Societe Chimique Pointet-Girard, Villeneuve-La-Garenne-France. Specific examples of the activation of pendant hydroxy groups by carbonyldimidazole are reported in J. Biol Chem (1979) 254:2572 and J. Chromatogr, (1981) 219:353–361. The activation of pendent carboxylic acid groups by water soluble carbodiimide is described in Biochem J. (1981) 199:297–419. Activation of carboxylic acids by N-hydroxysuccinimide is described in Biochemistry (1972) 111:2291 and Biophys. Acta (1981) 670:163.

Typical water-soluble polymers that may be activated by these procedures may include polyhydroxyethyl methacrylate and acrylate, methylvinylether copolymers, polyvinyl alcohols and copolymers, and the polyampholytes described above. Other water-soluble polymers may also be used.

Polymer Crosslinking

The analyte-responsive polymers of the present invention may be crosslinked by several mechanisms where the carboxylic acid moiety is the reactive site. Crosslinking may occur by reaction of pendant carboxylic acid groups with multifunctional aziridines or they my be crosslinked through pendant carboxylic acid groups by reaction with multifunctional epoxides. This reaction is typified by the crosslinking of 1,4-butanediol diglycidyl ether where the ring opening mechanism is similar to that of the reaction of aziridines. Alternatively, pendant primary amine groups can be formed on the analyte-responsive polymers by reaction of a few carboxylic acid groups with propyleneimine or ethyleneimine, which will allow the polymers to be crosslinked by reaction with a number of crosslinkers normally used in photographic systems for crosslinking gelatin such as aldehydes, carbodiimides, and others. A number of crosslinkers and crosslinking reactions used to crosslink gelatin, also capable of crosslinking the analyte-responsive polymers of the present invention through either acid or primary amine functionality are described in Pouradier and Burness (In the Theory of The Photographic Process, 3rd ed., C. E. K. Mees, Ed., pg. 54–60), herein incorporated by reference. Less commonly used but equally applicable are methods involving ionic crosslinking through metal ion coordination and reaction of ionic clusters, as well as various types of covalent bonding involving reaction of aziridines and Michael addition of olefins. For the analyte-responsive polymers of the present invention crosslinking or the pendant carboxylic acid groups with multifunctional aziridines is most preferred.

Growth Media

The basic growth medium for the invention contains nutrient materials selected for fermentation by the specific type cells to be analyzed. A specific analyte-responsive polymer (ARP) of the type described above is non-reactive with the medium alone. The medium can he optionally supplemented with growth regulators such as antibiotics, amino acids, vitamins, salts, or lipids. The growth regulators, such as hormones, used separately or in combination, may be used to make the medium either highly selective for a specific cell type or less selective for a broad spectrum cell response. The composition of the nutrient medium enables the invention to respond flexibly to a variety of analytical needs. Components for growth media are commercially available from Difco (Detroit, Mich.) and BBL (Coclceysville, Md.) among other sources. A detailed description of the growth media needed to practice the instant invention is reviewed by Ebersole et al. (Int'l. Pub. No. WO 91/01381) herein incorporated by reference.

Before testing or following sterilization, the pH of the nutrient medium was adjusted as needed to a value compatible with the physiological requirements of the cell culture and the propagational stability of the polymer.

Cell Concentration Determination

Cell concentration in a given experiment was estimated microscopically in a Petroff-Hauser counting chamber. Growth of the cell culture was first arrested by the addition of 0.1% sodium azide solution. In some cases, the cell densities in the Petroff-Hauser counting chamber were counted automatically using an Olympus Q2 image analyzer equipped with a Compaq 386/25 computer.

Piezoelectric Biosensor Device and System

Cell detection and identification, antibiotic response studies, and growth rate determinations can be made either with a single piezoelectric oscillator device under the conditions outlined above or with a piezoelectric oscillator device referenced against a second quartz crystal that compensates for instabilities associated with temperature. Such a device is described by Ebersole et al. (Int'l. Pub. No. WO 91/01381) and is herein incorporated by reference.

Use of Impedance analysis

The interaction of the polymer with the surface of the QCM is mechanical in nature and may be analyzed by impedance analysis. Impedance analysis measures the current across the quartz crystal at a constant voltage over a specified range Of frequencies. Impedance analysis was performed with a Hewlett-Packard 4194A Impedance/Gain-Phase Analyzer (HPIB) capable of performing measurements over a frequency range of 100 Hz–40 MHz in the impedance mode. Data collection was accomplished via an HPIB interface with a Macintosh personal computer. Impedance analysis is a technique well known to those skilled in the art and is outlined in Muramatsu et al., Anal. Chem., 60:2142 (1988) herein incorporated by reference.

Measurements of Refractive Index

An alternative detection system to acoustic sensors are optical devices capable of detecting changes in the refractive indices of polymer films. In the present invention analyte-receptor binding will produce small changes in effective index of refraction ($n_{eff}$) of the analyte-responsive polymer immobilized on a surface. The most preferred method of refractive indices measurement makes use of optical fibers and a single mode Mach-Zehnder interferometer in which the guided light is split into two parallel arms. One arm of the interferometer is coated with an analyte receptor while the other arm is protected to provide a reference path. As a result, light conducted into the waveguide is split into two beams. When analyte binding occurs, the refractive index at the surface of the receptor coated arm is altered whereas the effective index of the second beam (reference arm) does not change. When light in the interferometer arms are recombined, constructive or destructive interference can occur. If the arms of the interferometer are the same length (L1=L2=L), the difference in light propagation ($\Delta\Phi$) resulting from analyte binding can be mathematically described by equation 2, where $\lambda$ is the wavelength of input light, L is the path length, and n1 and n2 are the index of the reference and test arms respectively.

$$\Delta\Phi = \frac{2\Pi L}{\lambda}(n2-n1) \qquad \text{Eq. 2}$$

The phase difference is directly proportional to the difference in effective index difference (n2−n1) of the waveguide legs. Since the extent of analyte binding affects the $n_{eff}$=(n2−n1), the output intensity of the interferometer can be related to index changes resulting from the refraction induced by analyte binding. Devices that measure the changes in refractive indices of an analyte-responsive polymer film provide versatile transduction methods capable of detecting both direct analyte binding events as well as enzyme amplified analyte binding.

EXAMPLES

The following non-limiting examples illustrate the basic principles and unique advantages of the present invention.

Example 1

Procedure for Crosslinking Polyampholytes with Multi-functional Aziridines and Demonstration of pH-controlled Dye Binding Test solutions of polyampholyte and multi-functional aziridine crosslinker (Xama-7®) having ratios of 1:1, 5:1, 10:1, 50:1 and 100:1 polymer acid to aziridine were prepared by mixing stock solutions of 0.154 Normal (1-1-1) AA-MMA-DMAEMA polyampholyte (pI=7.0 in 20% methanol/water acidified to pH=6.0 with HCl) and 1.405 Normal Xama-7®. Before mixing the stock solutions, sufficient ammonium hydroxide was added to the polymer solution to shift the pH above 11.0 to prevent premature reaction of the aziridine with the polymer acid. The mixtures were then spin coated onto glass plates and piezoelectric crystals at rotor speeds of 1000, 2000 and 4000 rpm. The coated materials were then placed into a circulating air oven for 5 min at 100° C. to drive off the ammonia and cure the composition.

The plates were washed in water and tested for physical integrity. Coatings formed from the 1:1 and 5:1 mixtures were hard and essentially unswollen. The 10:1 and 50:1 compositions gave insoluble but swollen gel coatings with good adhesion to support, physical integrity and robustness. The 100:1 gel showed poor integrity and was easily abraded from the support. Therefore, the 10:1 and 50:1 compositions were chosen for further study.

The thickness of 50:1 coatings, as measured by elipsometry, were 0.2 µm, 0.4 µm and 0.8 µm for spin castings made at 4000, 2000, and 1000 rpm respectively. The charge on the surface of each film was demonstrated by placing a series of buffers, each containing an identical anionic blue dye, on each coated composition. After allowing the compositions to sit for 30 min, the compositions were washed with neutral water to remove unattached or unabsorbed dye. All dye spots corresponding to buffers with pK <7.0 remained easily detectable while all spots corresponding to buffers having pK >7.0 washed immediately from the coating. This was in spite of the fact that the basic buffers swelled the compositions as well as the acidic buffers. This demonstrates the pH-controlled dye binding characteristic of the polyampholyte coating.

The coated piezoelectric crystals prepared as described above were tested for microbial and enzymatic response and used in the following Examples concerning detection by piezoelectric means.

Example 2

Polymer Preparation and Immobilization

Figure 3:
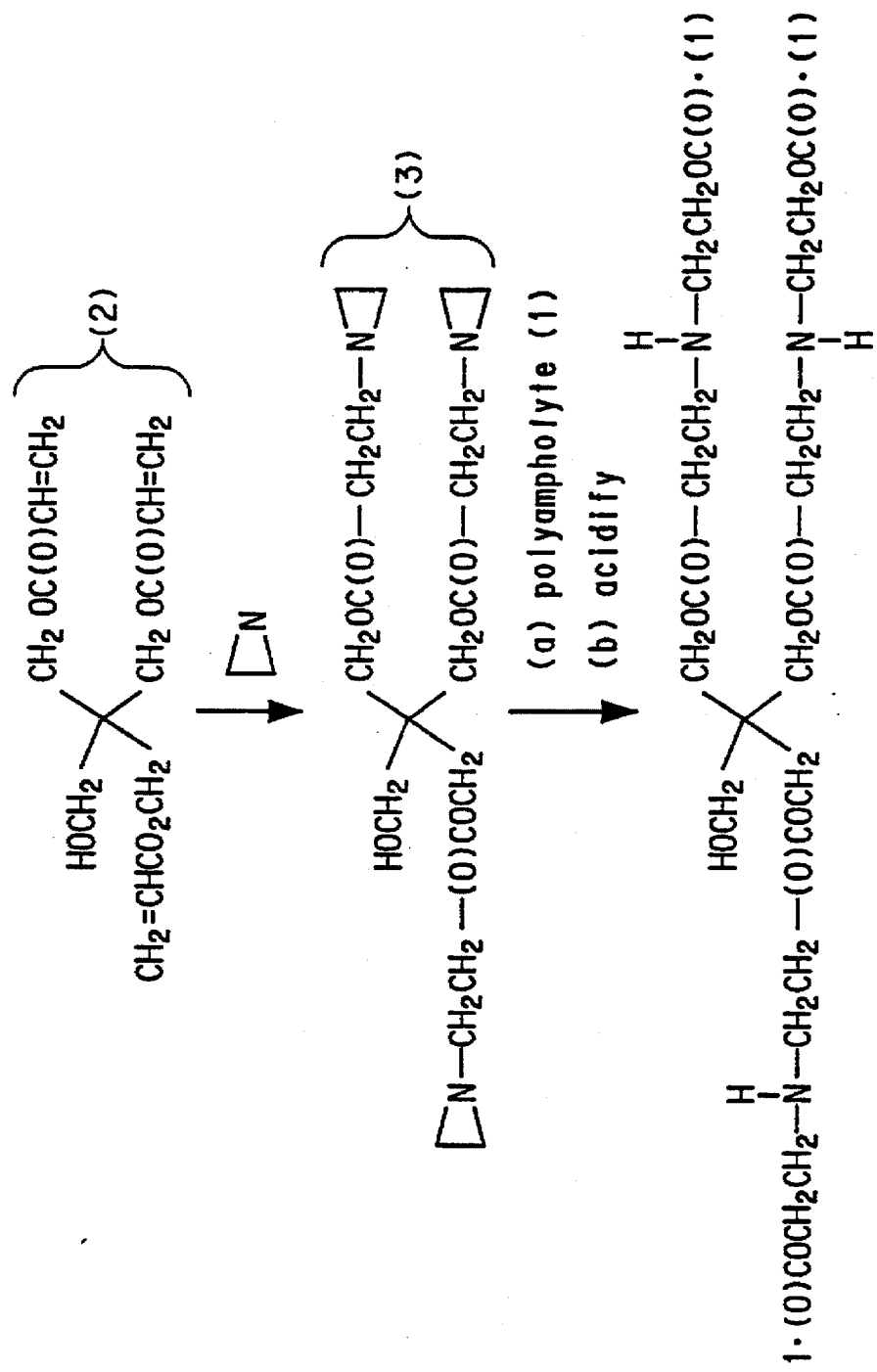
FIG. 3 illustrates a typical scheme for the preparation of a crosslinked analyte-responsive polymer.

The polymer (1) of FIG. 3 was synthesized according to the procedure of outline by Foss (U.S. Pat. No. 4,749,762) and by the following procedure. Under a nitrogen atmosphere, emulsifier solution (1000 mL distilled water, 10 g TRITON® QS-30 surfactant (Rohm & Haas, Philadelphia, Pa.) and 10 g N,N-dimethylaminoethanol) was heated to 60° C. Then a mixture containing 53 mL of methyl acrylate, 53 mL of methyl methacrylate, and 98 mL of N,N-dimethylaminoethyl methacrylate was added at 4 mL/min. When the solution became saturated (saturation is evident when the solution begins to exhibit translucency), an initiator solution (5 g of ammonium persulfate in 250 mL distilled water) was added at 0.75 mL/min while simultaneously continuing the momomer addition. Addition of the initiator solution resulted in immediate polymerization as evidenced by a temperature increase. After all the monomer was added, the mixture was stirred for an additional 15 min, and was then poured into a 2 L polyethylene beaker. Acetone was added until the product coagulated. The product was then collected by filtration and washed with water to remove remaining emulsifier and other impurities. The polymer was transferred to a flask equipped with a high shear blade stirrer, 800 mL ethanol was added and the mixture heated to 80° C. After the polymer had dissolved, a solution of 32.65 g KOH in 100 mL distilled water was added via an addition funnel in order to selectively hydrolyze the methyl methacrylate to the acrylic acid salt. The addition rate was controlled so that the polymer did not precipitate during this step. After the addition was complete, the mixture was stirred for an additional 30 min at 80° C. The product was isolated and purified by isoelectric precipitation. This was done by transferring the ethanolic polymer solution into a large excess of distilled water and then adding an equivalent amount of hydrochloric acid to shift the solution pH to the polymer's isoelectric point (pI). The polymer was then isolated by centrifugation, washed with water buffered at the pI and redissolved in water containing a small amount of ethanol at a pH either above or below the pI. The polymer was stored in this slightly acidic or basic solution because if isolated and dried at its pI, redissolving was slow and difficult.

Each side of an AT-cut quartz crystal was coated with 2000 Å thick gold electrodes. Underlayers of 500 Å thick titanium were used for adhesion in the center of the quartz crystal. One side of the crystal was spin-coated with the crosslinking polymer solution at 1000 rpm for 40 sec. The composite resonator thus formed was allowed to dry in air and was then heated at 100° C. for 10 min. in a circulating air oven.

Example 3

Polyampholyte Crosslinking

Films of polyampholyte (1) (FIG. 3) were crosslinked with a multifunctional aziridine according to the procedure depicted in FIG. 3. The crosslinker, pentaerythritol-tris-(B-aziridinyl)propionate (3) (Xama-7®), is prepared by the Michael addition of ethylene imine to pentaerythritol triacrylate (2). Crosslinked films of polyampholyte (1) were then prepared by spin-coating onto a support a solution containing 5.44% of polyampholyte (1) and a required amount of Composition (3), made basic with ammonium hydroxide to block premature crosslinking. The films were then crosslinked in place by mild heating for 5 min. at 100° C. It was found that generally a 50:1 equivalent ratio of 1:3 gave best results. The heating step eliminates $NH_3$, thereby allowing the coating to become mildly acidic thus enabling crosslinking of the polymer via a proton-assisted ring-opening reaction between the aziridine groups of the crosslinker and a small number of $-CO_2H$ groups of polyampholyte (1). The film thickness was controlled by spin-coating rotational speeds, which ranged from 1000–4000 rpm. Film thicknesses were determined independently with a Sloan Dektat IIA stylus profilometer.

Example 4

Piezoelectric ARP-Polymer Response to pH Change

This example illustrates that changes in pH of the test medium alter the properties of the crosslinked ARP. The resulting changes can be detected as alterations of ARP thickness, contact angle, and viscoelastic properties as reflected by alterations in piezoelectric oscillator response. Measurements of pH were made simultaneously by frequency measurements or network analysis and a Beckman Model O32 pH meter. The analog output of the pH meter was connected to an IO/Tech analog-digital converter interfaced to the HPIB, enabling automatic measurement of pH. Sessile contact angle measurements were performed with a Rame-Hart contact angle goniometer using a 10 µL water droplet.

Film thicknesses in aqueous solutions were measured directly with a phase measurement interferometric microscopy (PMIM) (Zygo, Inc.). Crosslinked films were coated on evaporated gold films on quartz substrates according to the procedure described in Example 3 and were immersed under a thin film (ca. 1 mm) of water that was contained with a glass cover slip. The pH of the solution was changed by replacing the water between the sample and the cover slip with water adjusted to the desirable pH value. A reference height difference for calibration was provided by the gold films, whose thickness was established from the frequency shift of the quartz crystal microbalance during electron beam vaporation.

Figure 4A:
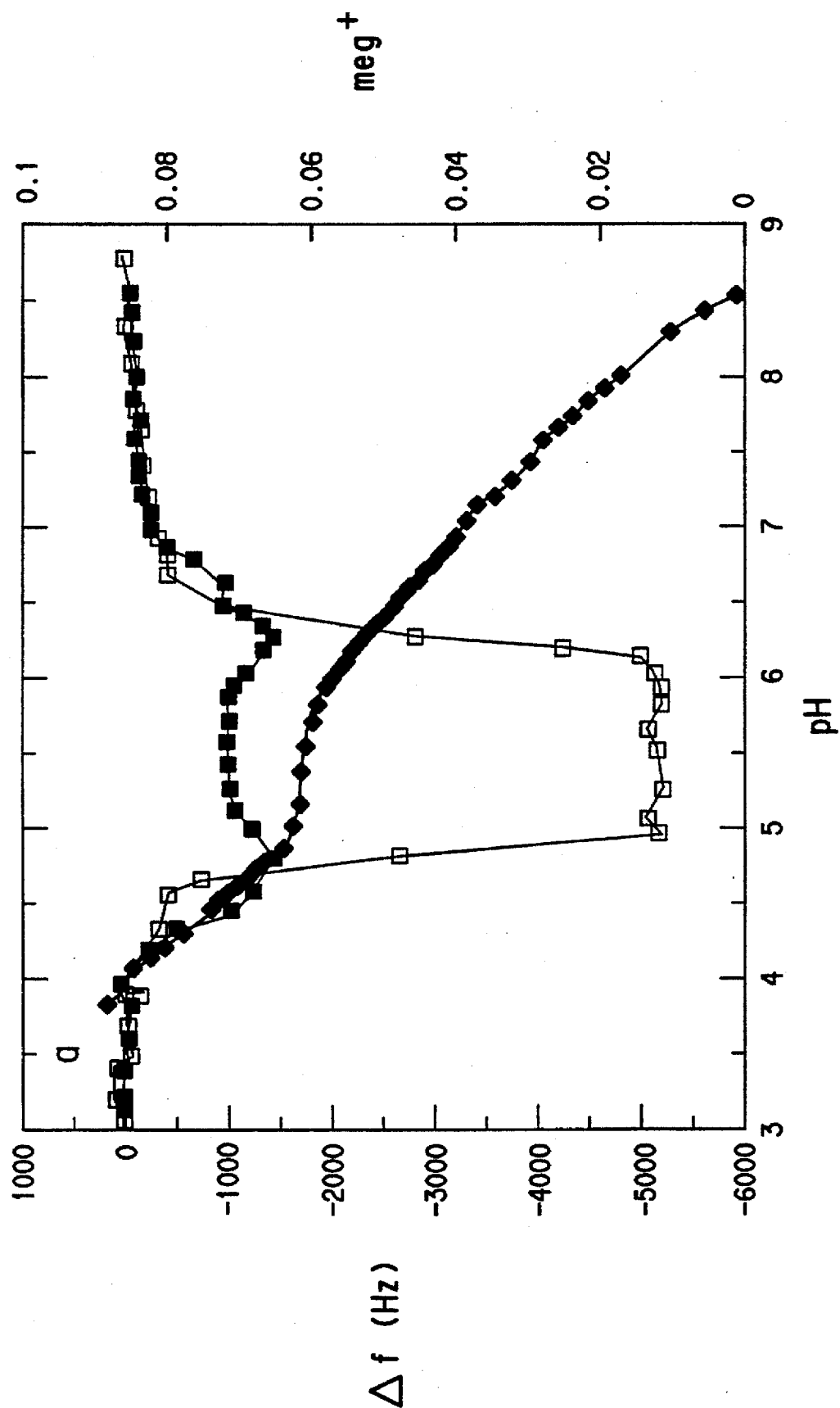
FIG. 4(a) illustrates the change in $f_{Gmax}$ at different pH values for a 5 MHz AT-cut quartz resonator coated with crosslinked polymer films. (■) film thickness=0.4 µm, (□) film thickness=0.8 µm.
Figure 4B:
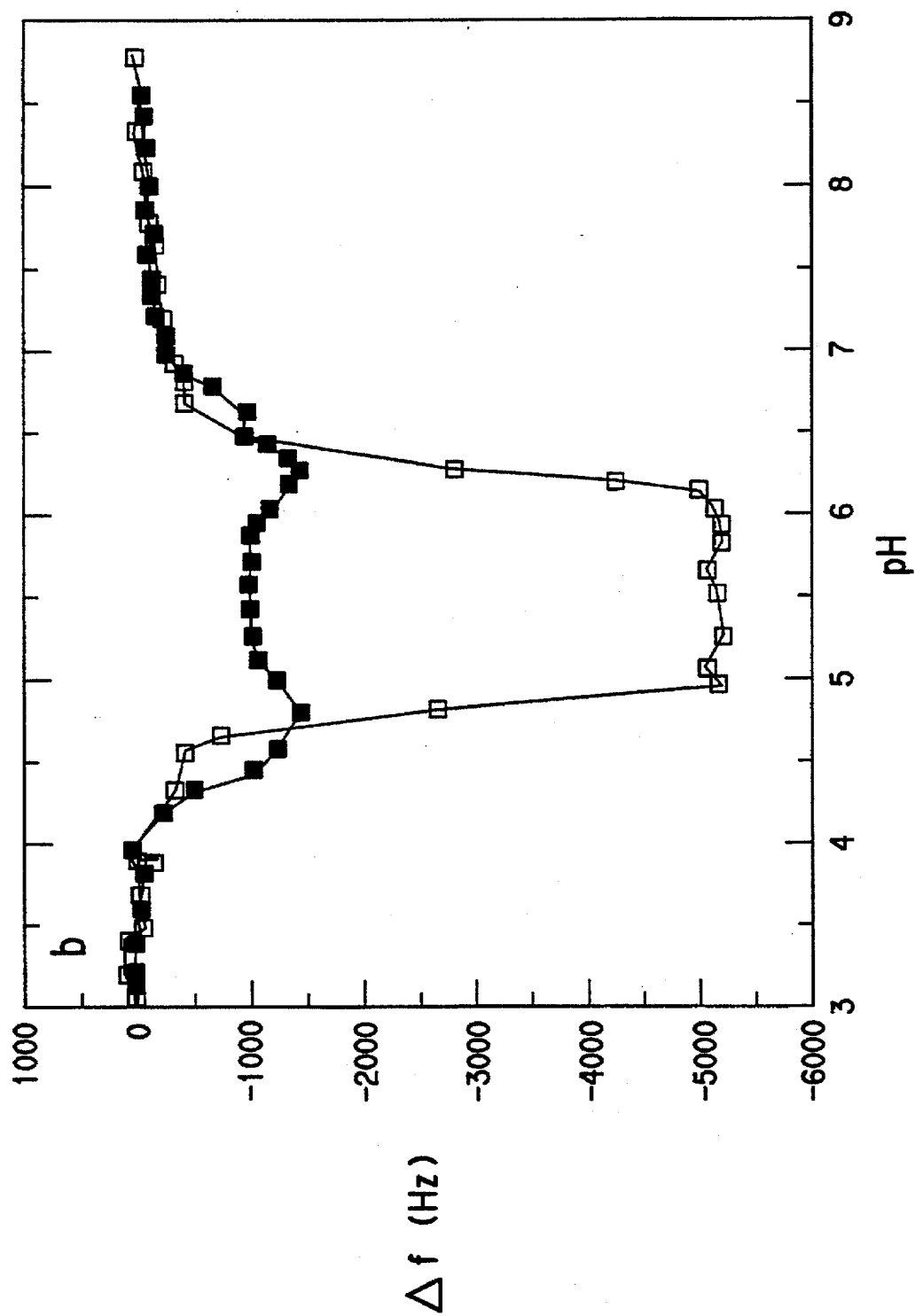
FIG. 4(b) illustrates the change in $f_{Gmax}$ at different pH values for a 5 MHz AT-cut quartz resonator coated with crosslinked polymer films. (■) film thickness=0.4 µm, (□) film thickness=0.8 µm.

In this example, the pH of the test mileu covering QCMs on which a 1:1:1 AA-MMA-DMAEMA crosslinked ARP immobilized as described above, was acidified with 0.001N HCl over the pH range of 9.0 to 3.0. Films of thicknesses of 0.8 µm and 0.4 µm respectively of were analyzed. The series resonant frequency (fs) measured with the composite resonator in the feedback loop of a broad-band amplifier, and the frequency of maximum conductance ($f_{Gmax}$) measured by impedance analysis, were found to change significantly when the pH of the solution exposed to the resonator was altered. (It is assumed throughout that the difference between fs and $f_{Gmax}$ is negligible). When the pH of the medium was gradually increased from pH=3.0, an abrupt frequency decrease was observed at pH=4.8 (FIGS. 4a and 4b). The magnitude of the frequency shift increased with polymer film thickness, giving exceptionally large shifts approaching −6000 Hz for 0.8 µm thick polymer film. The resonant frequency exhibited a slight increase at pH=5.5, followed by an abrupt increase at pH>6.1. The increase in the center of the isoelectrio region pH=5.5 was more apparent for the thinner films (0.4 µm), which also exhibited a broader isoelectric region based on the frequency changes. These data strongly suggest that the observed frequency changes were related to the changes accompanying the transitions between the ionic and isoelectric forms of the polymer. In addition, the frequency changes for the 0.4 and 0.8 µm thick films correspond to mass changes of approximately 20 µg $cm^{-2}$ and 90 µg $cm^{-2}$ which is substantially larger than the total areal mass (Δm/A) of these films after spin coating.

Example 5

Urease Activity Piezoelectric Measurement by ARP-OCM

The response to pH changes induced by urease-catalyzed hydrolysis of urea was measured in 2 mL of a buffer solution in which the resonator coated with crosslinked polymer 1 (FIG. 3) was immersed. The buffer solution was prepared from 1.48 mL 1.0 mM NaOH, 8 mL 0.2 mM EDTA and 100 mL of deionized water adjusted to a pH of 5.5 with phosphoric acid. Measurements of the pH changes dependent upon urease concentration were performed by adding known amounts of a urease solution (1 mg urease (Sigma, St. Louis, Mo.) in 100 mL of deionized water) to the buffer solution containing 0.25M urea (Fisher Scientific Co., Mo.) while the resonator was immersed in the solution. Conversely, the response dependence upon urea was determined by adding known amounts of a urea solution to the buffer solution containing 0.1 µg/mL urease.

Figure 5:
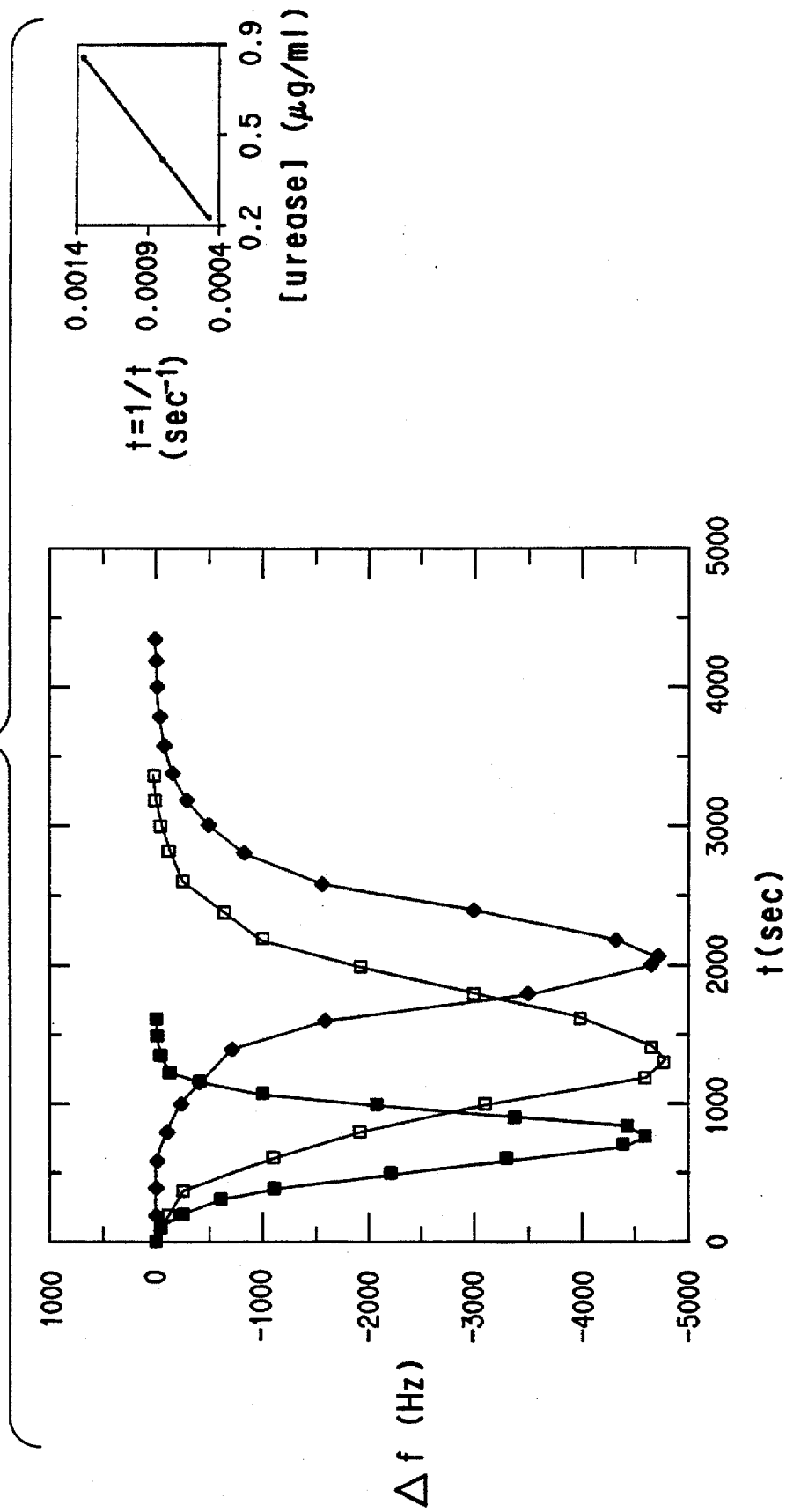
FIG. 5 illustrates the frequency response of a 5 MHz AT-cut resonator coated with a crosslinked polymer film to the urease-catalyzed hydrolysis of urea at three different urease concentrations: 0.83 µg/mL (small filled square), 0.43 µg/mL (open square) 0.22 µg/mL (larger filled square). Inset: Dependence of the time of minimum frequency on urease concentration.

Urease-catalyzed hydrolysis of urea results in the formation of $NH_3$ with a corresponding increase in the pH of the medium. Accordingly, when urea was added to a phosphate buffer solution (initial pH=4.0) containing urease, a monotonic frequency decrease is observed after a short time followed by a monotonic increase until the original frequency was attained (FIG. 5). The rates of frequency change in both branches were essentially identical. The time at which the frequency reached the minimum shifted to longer values with decreasing urease concentration. This data is consistent with pH-dependent frequency of the composite resonator: urease-catalyzed hydrolysis increases the pH of the medium resulting in conversion of the polymer/analyte complex to its isoelectric form where the frequency decreases. After the pH exceeded the pI the forequency increased once again.

Example 6

Measure of Microbe Metabolism by ARP-OCM

The aqueous growth medium (pH=7.4) for microbe metabolism measurements contained 1.0% wt/v protease peptone No. 3 (Difco), 0.1% beef extract (Bacto), 0.002% Bromo Cresol Purple, 0.5% NaCl. This base medium was supplemented with carbohydrates (1% wt/v) where required and filtered through a 0.2 µm Corning sterilization membrane. Response of the piezoelectric sensor to bacterial metabolism was investigated using reference strains obtained from the American Type Culture Collection (ATCC) (Rockville, Md.). *E. coli* (ATCC Accession No. 25922) was first grown overnight in a 3% trypticase soy broth (TSB) medium at 37° C. to a density of approximately $10^9$ cells/mL. Just before use, the cells were diluted to a minimal media composed of 1 part in 20 in Difco Bacto Purple broth (BPB) containing no carbohydrates. The cell density was determined microscopically in a haemocytometer using a light microscope. Portions of the diluted culture were then used as a starting inoculum for the piezoelectric sensor experiments. Four separate cultures of *E. coli* (one control and three experimental) were inoculated in TSB medium containing either inositol or one of three different carbohydrate supplements. The control culture contained inositol (1% wt/v) and the three experimental cultures contained either lactose manitol or arabinose at concentrations of 1% w/v. Cell numbers in aliquots removed from the QCM growth chamber were obtained by first arresting the cell growth of the aliquot by addition of a 0.1% sodium azide solution. The samples were vortexed and counted visually in a Petroff Hauser counting chamber. In some cases the cell concentrations were counted automatically using an Olympus Q2 image analyzer equipped with a Compaq 386/25 computer.

Figure 6:
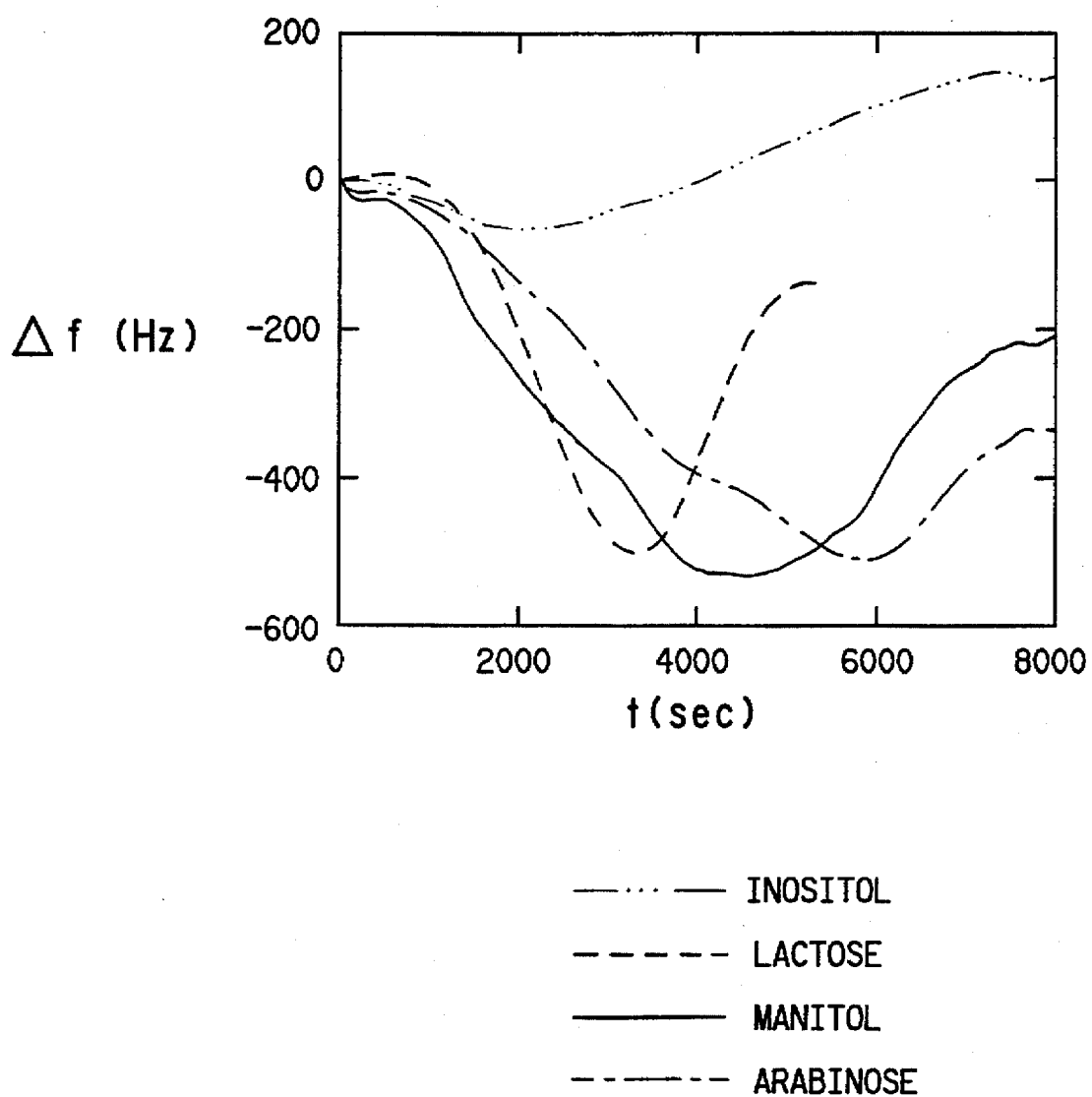
FIG. 6 illustrates the frequency response of a 5 MHz AT-cut resonator coated with a crosslinked polymer film to E. coli in different carbohydrates.
Figure 7:
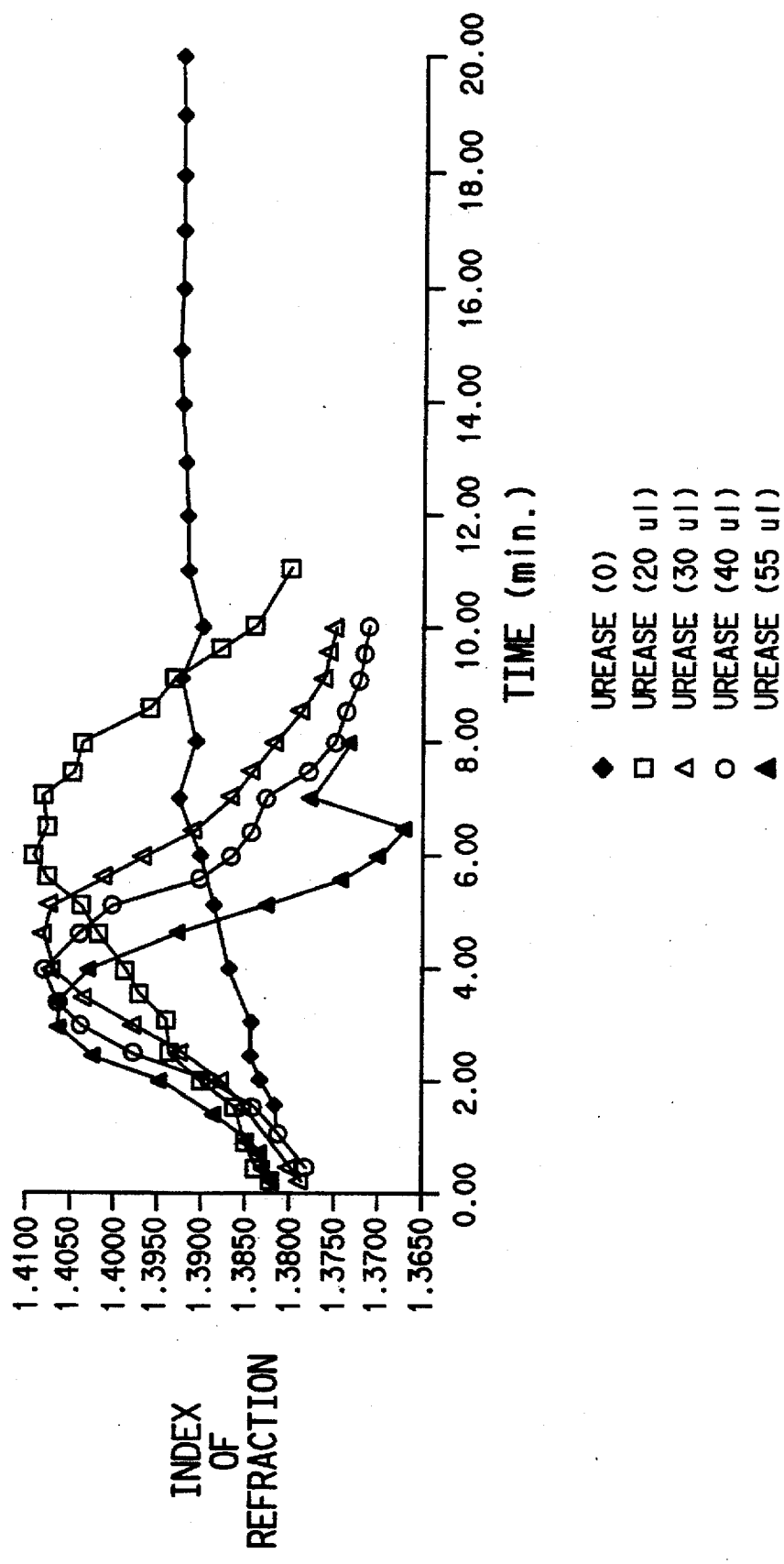
FIG. 7 illustrates the change in index of refraction of a crosslinked polymer film in response to the urease-catalyzed hydrolysis of urea at different urease concentrations over time.

Metabolic activity of microorganisms was seen to alter the pH of the growth medium. This occurred presumably as carbohydrates are converted into metabolites such as lactic acid, succinic acid, acetic acid or other acidic molecules. Cell metabolism rates were measured with the coated side of the composite resonator submerged in a growth medium containing carbohydrates. After an induction time (needed for the medium to reach the pH of the upper end of the isoelectric region of the polymer film), an initial decrease in medium pH was seen. This corresponded to a gradual decrease in the frequency of the QCM due to the formation of the isoelectric phase (FIG. 6). A gradual increase in the frequency relative to the initial frequency was then observed as the pH of the medium decreases through the isoelectric region. The time to the frequency minimum is inversely proportional to the metabolic and growth rate.

Example 7

Measurement of Refractive Index Changes Corresponding to pH Shift Through Polymer Isoelectric Point The purpose of this example was to demonstrate that a significant refractive index shift occurs that correlates with propagational changes observed with an ARP when the pH of their environment is shifted through the polymer's isoelectric point (pI). This response allows pH sensitive changes in the gels to be monitored by optical methods such as refractometers, modulation of evanescent coupling between parallel wave guides, or phase shifts in Mach-Zehnder type interferometers.

A nominal 1-1-1 AA-MMA-DMAEMA polyampholyte was purified by isoelectric precipitation in water by adjusting the pH to that of the polymer's isoelectric point. The precipitated polymer was washed with water buffered at pH 6.4, centrifuged, decanted, then redissolved in ethanol containing sufficient HCl to shift the pH to <4.0. The solids content of this solution (SP) was 0.1075 g polymer/g solution (0.327 meq acid/g solution).

A 0.1N solution of Xama-7® aziridine crosslinker (SX) was prepared by dissolving 0.712 g Xama-7® (142.3 g/eq) in 50 mL acetone.

A series of 100 mM phosphate buffer solutions were prepared at several pH's (6.0, 6.5, 7.0, 7.5 and 8.0), the pH range selected to span the isoelectric point of the amphoteric polymer matrix (Handbook of Chemistry and Physics).

Crosslinkable polymer solutions (C) with a theoretical crosslink density of 50 acid units/aziridine were prepared by mixing 1.0 mL of the stock polyampholyte solution (SP) with sufficient $NH_4OH$ to shift the pH to >10 to prevent premature reaction, and then adding 0.0653 mL of crosslinker solution (SX). The polymer solution was then coated directly on the prism of a Ziess Abby Refractometer using a 100 micron thickness metering rod and allowed to dry. The dried thickness was a nominal 1 micron. Following dry-down, the films were mildly heated for 5 min with a forced air blower. During dry-down and subsequent heating, ammonia was expelled and the polymer lightly crosslinked by the reaction of aziridine units with pendant carboxylic acid groups on the polymer.

The refractive index of the dried polymer was 1.5018 which is in agreement with typical acrylic polymers. A phosphate buffer solution, prepared as described above, was placed in contact with the polymer film and allowed to equilibrate. This was followed by the refractive index measurement. When the measurements were complete, the polymer gel could be removed by soaking with concentrated ammonium hydroxide and wiping the fractured gel from the prism. This allowed the prism to be used again for additional measurements with new polymer films. Additional polymer was then recast on the prism.

Refractive index measurements of the resultant compositions usually indicated the presence of two bands. One corresponded to the polymer gel and the other to aqueous media above the polymer. The refracive index band for the water interface was well defined in all cases. However, the polymer bands were well defined only in buffers approaching the isoelectric region of the polymer. Outside the isoelectric region, of pH between 7.5 and 5.0, the gel bands became extremely diffuse, to the point that they were not distinguishable when the pH was greater than 7.5 and less than 5.0. The results from these measurements are shown in Table B.

TABLE B

REFRACTIVE INDEX MEASUREMENTS ON CROSSLINKED ARP COMPOSITIONS vs. pH OF TEST MEDIA

| Buffer pH | n Polymer | n Buffer | Remarks |
|---|---|---|---|
| 8.0 | 1.3650 | 1.3345 | Very diffuse gel band |
| 7.5 | 1.3652 | 1.3348 | Diffuse gel band |
| 7.0 | 1.3728 | 1.3338 | Sharp, well defined bands |
| 6.5 | 1.3758 | 1.3336 | Sharp, well defined bands |
| 6.0 | 1.3780 | 1.3348 | Well defined bands |
| 5.5 | 1.3650 | 1.3340 | Very diffuse gel band |
| 5.0 | — | 1.3340 | Extremely diffuse gel band |
| 4.5 | — | 1.3340 | Extremely diffuse gel band |
| 4.0 | — | 1.3339 | Non-existent gel band |

The measurements showed a direct correlation between the refractive index of the amphoteric layer in response to pH variation. The polymer matrix may be expected to serve as good wave guides within their isoelectric region but become extremely poor outside this region. The pH induced changes in refractive index thus can be used to optically monitor pH correlated changes in cell growth, enzyme reactivity, or antigen-antibody responses.

Example 8

Measurement of Urease Activity by an APR-Optical Sensor

The following example demonstrates that urease activity can be measured by changes in the Refractive Index of an analyte-responsive polymer optical sensor.

Preparation of an analyte-responsive polymer optical sensor for urease was accomplished in the following manner. A nominal 1-1-1 AA-MMA-DMAEMA polyampholyte polymer was first purified by isoelectric precipitation in water by adjusting the pH to that of the polymer's isoelectric point (pI 6.4). The precipitated polymer was washed with water, buffered at pH 6.4, centrifuged, wash fluid decanted, and the precipitated polymer then redissolved in ethanol containing enough HCL to shift the pH to <4.0. The solid content of this solution was 0.107 g polymer/g of solution (0.327 meq. of acid polymer groups/g of solution).

A stock solution of Xama-7® aziridine crosslinker (SX) was prepared by dissolving 0.712 g Xama-7® (142 g/aziridine equivalent) in 50 mL of acetone. The Xama-7® stock solution was then mixed with the polymer solution to form a 50:1 mixture of polymer acid equivalents to aziridine equivalents. After mixing, one drop of conc. ammonium hydroxide was added to inhibit crosslinking and stablizie the coating solution until later use.

The crosslinking coating solution was then coated onto Fisher #1 25×25 mm glass microscope cover sheets (cat. #12-542C) using 20 μL of coating solution per coversheet. The polymer coatings were then air dried at room temp. and then cured in a vacuum oven at 130° C. for 20 min. The coversheets were then cooled to room temperature before use. Measurements of the dried polymer film coating indicated a dried layer of ca. 0.2 to 0.6 mm in thickness.

The crosslinked polymer coversheets were then mounted in a Carl Zeiss Model 27611 Refractometer using monobromonapthalene coupling fluid to optically connect the coversheet to the refractometer prism. For measurement of urease activity, a urea buffered substrate solution was prepared containing 0.2 mM EDTA, 100 mg urea, 1.4 mL of 0.1N NaOH dissolved in 100 mL of purified water. Before use, the pH of the solution was adjusted to pH 5.5. Varying concentrations of a Urease Enzyme Stock Solution (380 ug/mL) of Type C-3 Jack Bean urea amidohydrolase (EC 3.5.1.5) (Sigma, St.Louis, Mo.) in purified water was mixed with in 1.0 mL of urea substrate solution. The reaction fluids were then added immediately to the surface of the analyte-responsive polymer optical sensor and index of refraction measurements with time were then taken manually at room temperature over a period of time up to 30 min. (FIG. 8).

Refractive index measurements showed the presence of two interference bands. One band corresponded to the polymer interface and the other to the aqueous media above the analyte-responsive polymer surface. The water band remained well defined throughout the measurement, whereas the index band corresponding to the analyte-responsive polymer was sharply defined as the solution pH approached its isoelectric point. Beyond the isoelectric point (pH<5 to >7.5), the polymer index bands were diffuse.

Urease-catalyzed hydrolysis of urea results in the formation of $NH_3$ which increases the pH of the reaction solution. Accordingly, when the urease reaction mixture was added to the optical sensor, the index of refraction changed as the pH of the solution passed through the isoelectric point of the analyte-responsive polymer. Changes in index of refraction with time are shown as a function of varying urease concentrations in FIG. 8. Furthermore, as shown in Table C, the time required to reach maximum refractive index inversely decreased with the proportion of urease added to the reaction mixture.

TABLE C

| CORRELATION OF UREASE CONC. AND TIME TO MAXIMUM REFRACTIVE INDEX | | |
|---|---|---|
| Urease (μl) | RI-max Time (min.) | RI-max Range |
| 20 | 5.8 | 5.5–6.5 |
| 30 | 4.25 | 4.0–4.5 |
| 40 | 3.75 | 3.5–4.0 |
| 55 | 3.25 | 3.25–3.5 |

Example 9

The purpose of this example was to demonstrate 1) the attachment of an ARP to polystyrene plates, 2) attachment of antibody to the ARP, and 3) the use of an ARP in an antigen-antibody assay.

Part A) Determination of Minimum Polymer Coating Weight

As demonstrated in Example 1, the optimum ratio of active acid groups to aziridine crosslinker groups was determined to be 20:1 to 50:1. This ratio range reflects the molecular weight of the polyampholyte and the need to provide at least one crosslink per polymer chain. For this series of experiments the following reagent solutions were prepared and a ratio of 20:1 was chosen as the standard.

Test Solution A-1:1 Acid/Aziridine Concentrate

To 280 μL 0.1N Polyampholyte in 80:20 methanol/water solution (0.0328 g/mL - 1-1-1 AA-MMA-DMAEMA purified by isoelectric precipitation) was added 20 μL 1.405N Xama-7® in acetone and 20 μL concentrated $NH_4OH$. (Ammonium hydroxide was added in sufficient amount to block premature reaction of the aziridine with the acid groups on the polymer.)

Test Solution B-20:1 Coating Solution Concentrate

To 1.9 mL of 0.1N polyampholyte solution, used above, was added 0.1 mL Test Solution A. The solids content of this concentrate was 0.0328 g/mL.

Solutions were prepared as per Table D. Twenty μL portions were pipetted into 9 wells/row in a 96 well plate.

A different solution was placed in each row with row G left blank as control. Columns 10, 11, and 12 were also left blank.

Samples were force air dried at room temperature for 30 min and then placed in a vacuum oven at 35° C. overnight.

TABLE D

| COATING SOLUTIONS | | | | | |
|---|---|---|---|---|---|
| Sample # | mL B. | mL Water | $NH_4OH$ | Dilution | Conc. g/mL |
| 1 | 1 | 0 | 0.02 | 1.0 | 0.0328 |
| 2 | 5 | 5 | 0.02 | 0.5 | 0.0164 |
| 3 | 2 | 8 | 0.02 | 0.2 | 0.00656 |
| 4 | 1 | 9 | 0.02 | 0.1 | 0.0328 |
| 5 | 1 | 19 | 0.02 | 0.05 | 0.00164 |
| 6 | 1 (#4) | 9 | 0.02 | 0.01 | 0.000328 |

Binding Test

Buffer (pH=4) containing blue, red or green anionic dyes was placed in the wells. Dyes are chosen from water soluble dyes which can be mordanted by the amphoteric polymers and have at least one inonizable acidic group, such as, for example, —COOH or —$SO_3H$. Such dyes are well known in the art, as described, for example, in Miyazako, U.S. Pat. No. 3,795,519 and U.S. Pat. No. 5,107,063. Such dyes include, for example, acidic mono-, tri-, and pentamethine oxonols, carbo- and dicarbocyanines, merocyanines, indoleniums, azos, triphenylmethanes, tetrazines, and barbituric acids. Examples include: Oxonol Yello, Oxonol Red 536; Tartrazine; and Acid Violet 520T. As is well known to those skilled in the art, a dye whose absorption corresponds to the radiation to be absorbed will be chosen for use in the auxiliary layer. Buffer and blue dye was added to columns 1, 2, and 3. Buffer and red dye was added to columns 4, 5, and 6 and buffer and green dye was added to columns 7, 8, and 9. The polymer surfaces were soaked with 40 μL of dye/buffer solution for 30 min and then washed at room temperature with tap water. The adhesion of polymer to the wells and its concentration is demonstrated by the presence of absorbed dye in the polymer layer. Higher polymer concentrations gave a higher dye response. In all cases, good dye attachment was observed in wells containing up to and including the 100:1 dilution. The 20:1 dilution gave strong response with all dyes and appeared to give the best coating. Therefore, this coating composition was chosen for the antibody binding studies.

Part B) Antibody Attachment

A 20:1 acid to aziridine composition having a 20:1 dilution factor (0.00164 g/mL, 0.005N) was chosen for this experiment. The standard solutions were prepared as follows.

Antibody Stock Solution:

Goat anti-rabbit IgG (whole molecule was purchased from Sigma (St. Louis, Mo.). A stock solution of the antibody (2 mg/mL) was prepared by dissolving the entire contents of one vial (1 mg) in 0.5 mL of purified water. This yielded a stock antibody solution containing 2 mg/mL in a pH 7.2/0 mM sodium phosphate buffer containing 15 mM sodium chloride. This was used in combination with the following polyampholyte polymers and crosslinking reagents to prepare the following coating reagents.

Solution A-1:1 Super Concentrate

280 μL 0.1N 1-1-1 AA-MMA-DMAEMA polyampholyte in 80:20 methanol/water was combined with 20 μL NH$_4$OH and 20 μL 1.405N Xama-7® triaziridine in acetone.

Solution B-20:1 Coating Concentrate 1.9 mL 0.1N 1-1-1 AA-MMA-DMAEMA polyampholyte in 80:20 methanol/water was combined with 20 μL NH$_4$OH and 0.1 mL 1:1 Solution A (Super Concentrate).

Solution C-20:1—20:1 Coating Solution 0.1 mL (100 μL) of the 20:1 coating solution (Solution B) was diluted with 1.9 mL methanol containing 20 μL NH$_4$OH.

Solution D-0.14N Xama-7® Solution 0.1 mL of the 1.405 N Xama-7® stock solution was dissolved in 0.9 mL acetone.

Solution E-Antibody Solution #1

500 μL Ab Stock Solution was combined with 20 μL of Xama-7® solution D.

Solution F-Antibody Solution #2

1000 μL Ab Stock Solution was combined with 20 μL of Xama-7® solution D.

Coating Procedure

Every other column of each of two 96 well plates were coated with 20 μL of Coating Solution C. The plates were then air dried with a forced air blower for 30 min, then baked for 30 min in a vacuum oven at 50° C. A third plate was similarly coated except 20 μL of Coating Solution Concentrate B was used in place of C, thus giving a 20 fold excess of polymer in each well. Each plate was treated with antibody solution as shown in Tables E, F, and G below. After treatment the plates were tested by washing with phosphate buffer and then with Rabbit IgG colorimetric assay. Color changes were monitored using a thermomax Molecular Devices Corp. automatic colorimeter (Palo Alto, Calif.). Color responses were monitored for 10 and 20 min following addition of the assay reagents.

Plate #1

Columns 1, 3, 5, 7, 9, and 11 were coated with Solution C and dried. Petroleum ether was placed in each row as shown below in Table E, and 10 μL Ab Antibody Stock Solution was added to each well.

TABLE E

| Row | Petroleum Ether | Antibody Stock Solution | OD (10 min) Col. 1 | Col. 2 | Col. 3 | OD (20 min) Col. 1 | Col. 2 | Col. 3 |
|---|---|---|---|---|---|---|---|---|
| a | 200 μL Sol'n D | (10 μL) | .473 | .801 | .921 | .569 | .901 | 1.02 |
| b | 150 μL Sol'n D | (10 μL) | .613 | .956 | .669 | .693 | 1.07 | .745 |
| c | 100 μL Sol'n D | (10 μL) | .393 | .737 | .393 | .485 | .832 | .489 |

TABLE E-continued

| Row | Petroleum Ether | Antibody Stock Solution | OD (10 min) Col. 1 | Col. 2 | Col. 3 | OD (20 min) Col. 1 | Col. 2 | Col. 3 |
|---|---|---|---|---|---|---|---|---|
| d | 50 μL Sol'n D | (10 μL) | .457 | 1.27 | .420 | .539 | 1.35 | .524 |
| e | Control | (no Xama) | .077 | .048 | .073 | .200 | .218 | .187 |
| f | Blank | (10 μL) | .044 | .048 | .038 | .047 | .040 | .038 |
| g | Blank | (10 μL) | .039 | .040 | .033 | .054 | .039 | .048 |
| h | None | (10 μL) | .850 | .327 | .483 | .958 | .456 | .558 |

Plate #2

Columns 1, 3, 5, 7, 9, and 11 were coated with

Solution C and dried. Antibody solutions were placed directly in the well indicated below in Table F. No petroleum ether was used. The antibody solution contained aziridine which was allowed to react simultaneously with antibody and with the polymer interface.

Assay for Antibody Activity

The antibody activity in the above described test wells was determined by performing a sandwich immunoassay using a rabbit IgG (rIgG) test antigen and goat anti-r-IgG alkaline phosphatase conjugate enzyme reporter reagent. Reagents for this assay included:

Conjugate Stock Reagent-Goat Anti-RIgG (whole molecule) Alkaline Phosphatase Conjugate (Sigma, A-8025) was prepared by dissolving 5 μL of the sigma conjugate in 5 mL of the TRIS Sample Buffer.

Rabbit IgG Antigen Stock-A stock solution (100 ug/mL) of purified Rabbit IgG (Sigma, N.1-5006) was prepared by dissloving 0.5 mg in 5 mL of PBS. 20 μL of the stock was used in each well.

TRIS Sample Buffer-A Tris buffer (50 mM, pH 7.5), Sodium Chloride (75 mM), 0.1% SL-18 Detergent, 0.1% BSA and azide (0.02%) was prepared and stored at 4° C. This was used both as the diluent for the conjugate solution and the wash fluid.

Assay procedure-The antibody activity in test wells was assayed by:

1) Washing wells with Tris Sample Buffer. Each well was filled and the aspirated immediately. This process was repeated 3×.
2) 20 μL of the Rabbit IgG antigen stock solution was then added and the test solutions incubated at room temperature for 30 min. The Rabbit IgG was removed by aspiration.
3) Each test well was then washed three times with Sample Buffer.
4) Each test well was then incubated for 1 hr at room temperature with 20 μL of the anti-R-IgG conjugate stock solution. The conjugate reagent was then removed and each well was washed 4× with Tris Sample Buffer.
5) BCIP® Phosphatase substrate solution (Sigma, St. Louis, Mo.) (20 μL) was then added to each well and incubated at room temperature for 30 min. The color in the test wells were then read.

TABLE F

| Row | Antibody Sol'n | OD (10 min) | | | OD (20 min) | | |
|---|---|---|---|---|---|---|---|
| | | Col. 1 | Col. 2 | Col. 3 | Col. 1 | Col. 2 | Col. 3 |
| a | Sol'n E (10 μL) | .094 | .065 | .090 | .264 | .256 | .239 |
| b | Sol'n E (10 μL) | .082 | .077 | .091 | .216 | .271 | .247 |
| c | Sol'n E (10 μL) | .092 | .065 | .094 | .237 | .232 | .229 |
| d | Blank | .041 | .044 | .041 | .094 | .055 | .083 |
| e | Empty | .036 | .039 | .046 | .036 | .045 | .046 |
| f | Empty | .043 | .052 | .038 | .046 | .052 | .038 |
| g | Sol'n F (10 μL) | .143 | .054 | .101 | .316 | .221 | .246 |
| h | Sol'n F (10 μL) | .088 | .047 | .092 | .226 | .190 | .233 |

Plate #3

Columns 1, 3, 5, 7, 9, and 11 were coated with Solution B and dried. Antibody solutions were placed directly in the well indicated below in Table G. No petroleum ether was used. The antibody solution containing aziridine was allowed to react simultaneously with antibody and with the polymer interface.

TABLE G

| Row | Antibody Sol'n | OD (10 min) | | | OD (20 min) | | |
|---|---|---|---|---|---|---|---|
| | | Col. 1 | Col. 2 | Col. 3 | Col. 1 | Col. 2 | Col. 3 |
| a | Sol'n E (10 μL) | .036 | .064 | .042 | .113 | .229 | .092 |
| b | Sol'n E (10 μL) | .039 | .071 | .045 | .074 | .273 | .070 |
| c | Blank | .042 | .042 | .046 | .050 | .062 | .050 |
| d | Empty | .043 | .043 | .043 | .043 | .042 | .043 |
| e | Sol'n F (10 μL) | .071 | .056 | .044 | .190 | .265 | .127 |
| f | Sol'n F (10 μL) | .047 | .059 | .046 | .132 | .239 | .134 |

The results of these experiments shown in Tables E, F, and G clearly show that aziridine crosslinked polymer is securely bonded to the surfaces of the polystyrene plates. Antibody can be attached to the polymer by aziridine bonding either by 1) initially treating the polymer with aziridine to form a reactive surface toward the antibody or 2) by allowing the antibody to react with aziridine first and then allowing this complex to react with the polymer coated surface. In either case, the antibody retains antigen binding activity crosslinking and activated antibody does not bond to surfaces not treated initially with the polymer.

What is claimed is:

1. A method for detecting protons present in a liquid medium comprising the steps of:

(i) preparing a composite sensor comprising an amphoteric proton-responsive polymer, wherein said polymer has the ability to modulate between ionic and isoelectric forms in response to a proton, and wherein said amphoteric polymer is selected from the group consisting of amphoteric co- or terpolymers of pI between 5.0 to 8.0 of acrylic acid, methacrylate, and N,N dimethyl-aminoethyl methacrylate and wherein said polymer is immobilized on a surface of an acoustic sensor which is capable of detecting surface propagational changes, wherein said amphoteric proton-responsive polymer will produce propagational changes in response to the presence of said proton;

(ii) measuring the resonant frequency of said acoustic sensor, in a liquid medium;

(iii) contacting said composite sensor with a sample liquid medium suspected of containing said protons;

(iv) measuring the resonant frequency of said acoustic sensor to determine a change in resonant frequency wherein said change is comprised of first change consisting of either an increase or decrease in resonant frequency as the polymer approaches its isoelectric point followed by a second change in a direction opposite from said first change; and (v) correlating said changes in resonant frequency with the presence of said protons.

2. A method as recited in claim 1 wherein said acoustic sensor is a piezoelectric oscillator.

3. A method for measuring the change in concentration of protons present in a liquid medium comprising the steps of:

(i) preparing a composite sensor comprising an amphoteric proton-responsive polymer, wherein said polymer has the ability to modulate between ionic and isoelectric forms in response to a proton, immobilized on a surface of an acoustic sensor which is capable of detecting surface propagational changes, wherein said amphoteric proton-responsive polymer will produce propagational changes in response to a change in concentration of said proton and wherein said amphoteric polymer is selected from the group consisting of amphoteric co- or terpolymers of pI between 5.0 to 8.0 of acrylic acid, alkyl methacrylate, and N,N dimethyl-aminoethyl methacrylate;

(ii) measuring the resonant frequency of said acoustic sensor, in a liquid medium;

(iii) contacting said composite sensor with a sample liquid medium suspected of containing said protons;

(iv) measuring the resonant frequency of said acoustic sensor to determine a change in resonant frequency wherein said change is comprised of first change consisting of either an increase or decrease in resonant frequency as the polymer approaches its isoelectric point followed by a second change in a direction opposite from said first change; and (v) correlating said changes in resonant frequency with the change in proton concentration.

* * * * *